United States Patent [19]
Piwinski et al.

[11] Patent Number: 4,826,853
[45] Date of Patent: May 2, 1989

[54] 6,11-DIHYDRO-11-(N-SUBSTITUTED-4-PIPERIDYLIDENE)-5H-BENZO(5,6)CYCLOHEPTA(1,2-B)PYRIDINES AND COMPOSITIONS AND METHODS OF USE

[75] Inventors: John J. Piwinski, Parsippany; Ashit K. Ganguly, Upper Montclair; Michael J. Green, Skillman; Frank J. Villani, Fairfield; Jesse Wong, Union, all of N.J.

[73] Assignee: Schering Corporation, Kenilworth, N.J.

[21] Appl. No.: 925,342

[22] Filed: Oct. 31, 1986

[51] Int. Cl.[4] ................ C07D 401/04; A61K 31/445
[52] U.S. Cl. ..................................... 514/290; 546/93; 544/298; 544/316; 544/319; 544/320; 544/333; 544/361; 544/405; 514/253; 514/255; 514/269; 514/275
[58] Field of Search ................. 546/93; 544/298, 316, 544/319, 320, 333, 405, 361; 514/290, 253, 255, 269, 275

[56] References Cited

U.S. PATENT DOCUMENTS

| | | | |
|---|---|---|---|
| 3,326,924 | 6/1967 | Villani | 544/126 |
| 3,357,986 | 12/1967 | Villani | 546/93 |
| 3,409,621 | 11/1968 | Villani | 546/93 |
| 3,419,565 | 12/1968 | Villani | 546/93 |
| 3,717,647 | 2/1973 | Villani | 546/315 |
| 4,034,095 | 7/1977 | Bastian | 514/290 |
| 4,282,233 | 9/1981 | Villani | 546/93 |
| 4,355,036 | 10/1982 | Villani | 514/316 |

FOREIGN PATENT DOCUMENTS 0042544  3/1984  European Pat. Off. ............ 546/315

OTHER PUBLICATIONS

J. Med. Chem. vol. 15, No. 7, 750–754, (1972).

Primary Examiner—Mary C. Lee
Assistant Examiner—Zinna Northington
Attorney, Agent, or Firm—Henry P. Nowak; Richard C. Billups; James R. Nelson

[57] ABSTRACT

Derivatives of 6,11-dihydro-11-(4-piperidylidene)-5H-benzo[5,6]cyclohepta[1,2-b]pyridine, and pharmaceutically acceptable salts and solvates thereof are disclosed, which possess anti-allergic and anti-inflammatory activity. Methods for preparing and using the compounds are also described.

29 Claims, No Drawings

6,11-DIHYDRO-11-(N-SUBSTITUTED-4-PIPERIDYLIDENE)-5H-BENZO(5,6)CYCLOHEPTA(1,2-B)PYRIDINES AND COMPOSITIONS AND METHODS OF USE

BACKGROUND OF THE INVENTION

The present invention relates to 6,11-dihydro-11-(N-substituted-4-piperidylidene)-5H-benzo[5,6]cyclohepta[1,2-b]pyridines and to pharmaceutical compositions and methods of using such compounds.

U.S. Pat. Nos. 3,326,924, 3,717,647 and 4,282,233, European published Application No. 0042544 and Villani et al., *Journal of Medicinal Chemistry*, Vol. 15, No. 7, pp 750–754 (1972) describe certain 11-(4-piperidylidene)-5H-benzo[5,6]cyclohepta[1,2-b]pyridines as antihistamines. U.S. Pat. No. 4,355,036 describes certain N-substituted piperidylidene compounds.

SUMMARY OF THE INVENTION

The invention in its chemical compound aspect is a compound having the structural formula I:

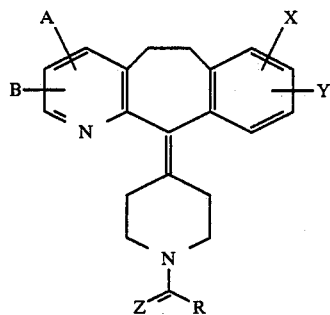

or a pharmaceutically acceptable salt or solvate thereof, wherein:

A, B, X and Y may be the same or different and each indepdently represents —H, halo, —CF$_3$, alkyl {which may be substituted with halo, OR$^1$ or COOR$^1$}, alkenyl, —OR$^1$, —COR$^1$, —SR$^1$, —N(R$^1$)$_2$, —NO$_2$, —O(CO)R$^1$, —COOR$^1$, or —O(CO)OR$^1$ (where each R$^1$ independently represents hydrogen, alkyl or aryl);

Z represents O, S or H$_2$ such that (a) when Z represents O, R represents —H, aryl, —D {wherein D represents a heterocycloalkyl group or a group selected from

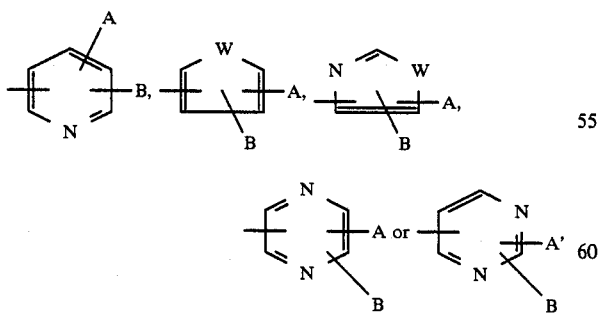

W represents O, S, or NR$^1$ (wherein R$^1$ is defined above)}, —SR$^2$ {wherein R$^2$ represents alkyl or aryl}, —N(R$^1$)$_2$, alkyl, cycloalkyl, alkenyl or alkynyl {which alkyl, cycloalkyl, alkenyl or alkynyl group may optionally be substituted with from 1 to 3 groups, each independently selected from halo, —CON(R$^1$)$_2$, aryl, —COOR$^1$, —OR$_3$, —SR$^3$, —N(R$^1$)$_2$, —COR$^3$, —NO$_2$ or —D, wherein R$^1$ and D are as previously defined and R$^3$ represents —R$^1$, —(CH$_2$)$_m$—OR$^1$ (wherein m=1, 2, 3, or 4) or —(CH$_2$)$_n$COOR$^1$ (wherein n represents 0, 1, 2, 3 or 4), with the proviso that said alkenyl or alkynyl group does not contain a —OH, —SH or —N(R$^1$)$_2$ group on a carbon atom of the carbon-carbon double bond or carbon-carbon triple bond, respectively, thereof};

(b) when Z represents S, R represents in addition to those R groups as defined in (a) above, aryloxy or alkoxy; and (c) when Z represents H$^2$, R represents —COOR$^1$, —E—COOR$^1$, or —E—OR$^3$, wherein E is alkanediyl which may be substituted with aryl, —OR$^1$, —SR$^1$, —N(R$^1$)$_2$ or —D, wherein R$^1$, R$^3$ and D are as previously defined.

In a preferred embodiment of the invention, Z represents O or S and R represents alkyl, cycloalkyl, alkenyl, aryl or alkyl substituted with —OR$_3$, —SR$_3$, —N(R$^1$)$_2$ or —COR$^3$. More preferably, when Z represents O or S, R represents alkyl having from 1 to 3 carbon atoms, cycloalkyl of from 3 to 6 carbon atoms, alkenyl of from 3 to 4 carbon atoms, or alkyl of from 1 to 3 carbon atoms substituted with —OR$^3$, —SR$^3$, —N(R$^1$)$_2$, or —COR$^3$. A, B, X and Y preferably represent H or halo, and more preferably one or both of X and Y is halo, e.g. chloro or fluoro, and A and B are H. The most preferred value of X is —F or —Cl, located at carbon atom 8 and/or 9, as shown in the following numbered ring structure:

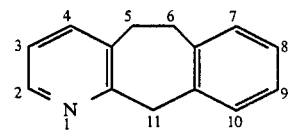

Preferably when Z is H$_2$, R is —E—COOR$^1$ or —E—OR$^3$.

Preferred compounds of the invention include:

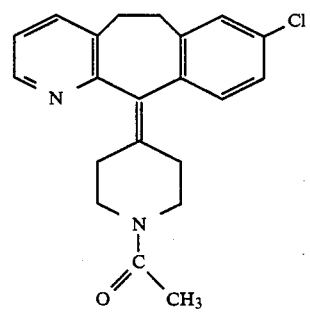

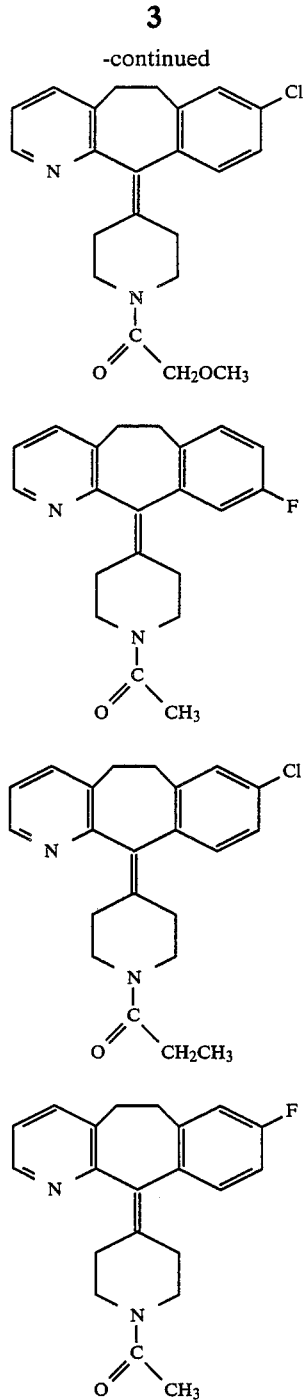

Additional species of compounds of the invention falling within the scope of formula I include:
11-(1-acetyl-4-piperidylidene)-6,11-dihydro-5H-benzo [5,6]cyclohepta[1,2-b]pyridine;
11-(1-methoxyacetyl-4-piperidylidene)-6,11-dihydro-5H-benzo [5,6]cyclohepta[1,2-b]pyridine;
11-(1-benzoyl-4-piperidylidene)-6,11-dihydro-5H-benzo [5,6]cyclohepta[1,2-b]pyridine;
11[1-(3-chlorophenylacetyl)-4-piperidylidene] 6,11-dihydro-5H-benzo[5,6]cylclohepta[1,2-]pyridine;
11-[1-(3,4-dimethoxybenzoyl)-4-piperidylidene] 6,11-dihydro -5H-benzo[5,6]cyclohepta[1,2-b]pyridine;
8-chloro-11-(1-acetyl-4-piperidylidene)-6,11-dihydro-5H-benzo [5,6]cyclohepta[1,2-b]pyridine;
8-chloro-11-(1-trimethylacetyl-4-piperidylidene)-6,11-dihyro-5H-benzo[5,6]-cyclohepta[1,2-b]pyridine;
8-chloro-11-[1-(tertiary butylacetyl)-4-piperidylidene]6,11-dihydro-5H-benzo [5,6]-cyclohepta[1,2-b]pyridine;
8-chloro-11-[1-(ethoxyacetyl)-4-piperidylidene]-6,11-dihydro-5H-benzo [5,6]-cyclohepta[1,2-b]pyridine;
8-chloro-11-[1-(2-hydroxypropionyl)-4-piperidylidene]-6,11-dihydro-5H-benzo[5,6]cyclohepta[1,2-b]pyridine;
9-chloro-11-(1-methoxyacetyl-4-piperidylidene)-6,11-dihydro-5H-benzo[5,6]-cyclohepta[1,2-b]pyridine;
8-chloro-11-[1-(2-methoxypropionyl)-4-piperidylidene]-6,11-dihydro-5H-benzo[5,6]-cyclohepta[1,2-b]pyridine;
8-chloro-11-[1-(1,2-propanedionyl)-4-piperidylidene]-6,11-dihydro-5H-benzo[5,6]-cyclohepta[1,2-b]pyridine;
8-chloro-11-[1-(1-ethoxyoxoacetyl)-4-piperidylidene]-6,11-dihydro-5H-benzo[5,6]-cyclohepta[1,2 -b]pyridine;
8-chloro-11-[1-(tertiarybutoxycarbonylaminoacetyl)-4-piperidylidene]-6,11-dihydro-5H-benzo[5,6]cyclohepta[1,2-b]pyridine;
8-chloro-11-(1-trifluoroacetyl-4-piperidylidene)-6,11-dihydro -5H-benzo[5,6]-cyclohepta[1,2-b]pyridine;
8-chloro-11-(1-benzoyl-4-piperidylidene)-6,11-dihydro-5H-benzo[5,6]cyclohepta[1,2-b]pyridine;
8-chloro-11-[1-(3,4,5-trimethoxybenzoyl)-4-piperidylidene]-6,11-dihydro-5H-benzo[5,6]-cyclohepta[1,2-b]pyridine;
8-fluoro-11-(1-butyryl-4-piperidylidene)-6,11-dihydro-5H-benzo[5,6]cyclohepta[1,2-b]pyridine;
8-fluoro-11-(1-methoxyacetyl-4-piperidylidene)-6 ,11-dihydro-5H-benzo[5,6]-cyclohepta[1,2-b]pyridine;
9-fluoro-11-(1-methoxyacetyl-4-piperidylidene)-6,11-dihydro-5H-benzo[5,6]-cyclohepta[1,2-b]pyridine;
8,9-difluoro-11-(1-methoxyacetyl-4-piperidylidene)-6,11-dihydro-5h-benzo[5,6]-cyclohepta[1,2-b]pyridine;
8-methyl-11-(1-methoxyacetyl-4-piperidylidene)-6,11-dihydro-5H-benzo[5,6]cyclohepta[1,2-9 pyridine;
8-chloro-11-(1-cyclopropylcarbonyl-4-piperidylidene)-6, 11-dihydro-5H-benzo[5,6]cyclohepta[1,2-9 pyridine;
8-chloro-11-(1-butyryl-4-piperidylidene)-6,11-dihydro-5H-benzo [5,6]cyclohepta[1,2-b]pyridine;
8-methoxy-11-(1-acetyl-4-piperidylidene)-6,11-dihydro-5H-benzo [5,6]cyclohepta[1,2-b]pyridine;
9-chloro-11-(1-acetyl-4-piperidylidene)-6,11-dihydro-5H-benzo [5,6]cyclohepta[1,2-b]pyridine;
8,9-difluoro-11-(1-acetyl-4-piperidylidene)-6,11-dihydro-5H-benzo [5,6]cyclohepta[1,2-b]pyridine;
8-methyl-11-(1-acetyl-4-piperidylidene)-6,11-dihydro-5H-benzo [5,6]cyclohepta[1,2-b]pyridine;
8,9-dichloro-11-1(1-acetyl-4-piperidylidene)-6,11-dihydro-5H-benzo [5,6 cyclohepta[1,2-b pyridine;
8-chloro-11-[1-(2-(2-hydroxyethoxy)ethyl)-4-piperidylidene]-6,11-dihydro-5H-benzo[5,6]cyclohepta [1,2-b]pyridine;
8-chloro-11-[1-[4-(4-butylphenyl)4-hydroxybutyl]-4-piperidylidene]-6,11-dihydro-5H-benzo[5,6]cyclohepta[1,2-b]pyridine;
8-chloro-11-(1-aminoacetyl-4-piperidylidene)-6,11-dihydro-5H-benzo[5,6]cyclohepta[1,2-b]pyridine;
8-chloro-11-(1-formyl-4-piperidylidene)-6,11-dihydro-5H-benzo[5,6]cyclohepta[1,2-b]pyridine;

8-chloro-11-(1-phenylthiocarbonylmethyl-4-piperidylidene)-6,11-dihydro-5H-benzo[5,6]cyclohepta[1,2-b]pyridine;

8-chloro-11-[1-(1-thiocarbonylethyl)-4-piperidylidene]-6,11-dihydro-5H-benzo[5,6]cyclohepta[1,2-b]pyridine; and 8-chloro-11-[1-[(ethylthio)carbonyl]-4-piperidylidene]-6,11-dihydro-5H-benzo[5,6]cyclohepta[1,2-b]pyridine.

The invention also involves a composition which comprises a compound of formula I as defined above in combination with a pharmaceutically acceptable carrier.

The invention further involves a method of treating allergy or inflammation in a mammal which comprises administering the above defined compound of formula I to said mammal in an amount effective to treat allergy or inflammation, respectively.

As used herein, the following terms are used as defined below unless otherwise indicated:

alkyl—(including the alkyl portions of alkoxy, alkylamino and dialkylamino) represents straight and branched carbon chains and contains from one to twenty carbon atoms, preferably one to six carbon atoms;

alkanediyl—represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene, —CH$_2$CH$_2$CH$_2$—,

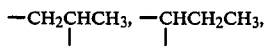

etc.

cycloalkyl—represents saturated carbocyclic rings branched or unbranched of from 3 to 20 carbon atoms, preferably 3 to 7 carbon atoms;

heterocycloalkyl—represents a saturated, branched or unbranched carbocyclic ring containing from 3 to 15 carbon atoms, preferably from 4 to 6 carbon atoms, which carboxyclic ring is interrupted by 1 to 3 hetero groups selected from —O—, —S— or —NR$^1$-(suitable heterocycloalkyl groups including 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc.);

alkenyl—represents straight and branched carbon chains having at least one carbon to carbon double bond and containing from 2 to 12 carbon atoms, preferably from 3 to 6 carbon atoms;

alkynyl—represents straight and branched carbon chains having at least one carbon to carbon triple bond and containing from 2 to 12 carbon atoms, preferably from 2 to 6 carbon atoms;

aryl (including the aryl portion of aryloxy)—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted with one or 1 more of halo, alkyl, hydroxy, alkoxy, phenoxy, amino, alkylamino, dialkylamino, —COOR$^1$ or —NO$_2$; and halo—represents fluoro, chloro, bromo and iodo.

DESCRIPTION OF THE INVENTION

Certain compounds of the invention may exist in isomeric forms. The invention contemplates all such isomers both in pure form and in admixture, including racemic mixtures.

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

As noted above, the pyridine and benzene ring structures of formula I may contain one or more substituents A, B, X and Y. Similarly, the heterocyclic ring D may contain one or more of A, B and X. In compounds where there is more than one such substituent, they may be the same or different. Thus compounds having combinations of such substituents are within the scope of the invention. Also, the lines drawn into the rings from the A, B, X and Y groups indicate that such groups may be attached at any of the available positions. For example, the A and B groups may be attached at the 2, 3 or 4 positions while the X and Y groups may be attached at any of the 7, 8, 9 or 10 positions.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salt and quaternary ammonium salts. For example, the pyrido- or pyrazino- nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The quaternary ammonium salts are prepared by conventional methods, e.g., by reaction of a tertiary amino group in a compound of formula I with a quaternizing compound such as an alkyl iodide, etc. The free base forms differ from their respective salt forms somewhat in certain physical properties, such as solubility in polar solvents, but the salts are otherwise equivalent to their respective free base forms for purposes of the invention.

All such acid, base and quaternary salts are intended to be pharmaceutically acceptable salts within the scope of the invention and all acid and base salts are considered equivalent to the free forms of the corresponding compounds for purposes of the invention.

The following processes A–C may be employed to produce compounds of general structural formula I.

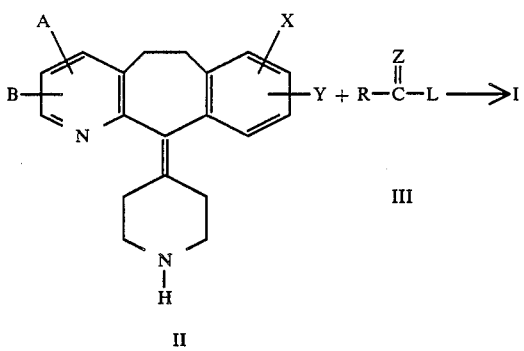

III

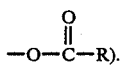

II

A. A compound of general formula II may be reacted with compound III in the presence of base to produce compounds of general structural formula I. Representative examples of appropriate bases are pyridine and triethylamine. L designates a suitable leaving group. For example, if Z is O or S, a compound of compound III may be an acyl halide (e.g., L=halo) or acyl anhydride, (e.g., L is $$-O-\overset{O}{\underset{\|}{C}}-R).$$

Alternatively, if the leaving group is hydroxy a coupling reagent may be employed to form Compound I. Examples of coupling agents include N,N'-dicyclohexylcarbodiimide (DCC) and N,N'-carbonyldiimidazole (CDI). The leaving group may also be alkoxy, in which case the compounds of formula I may be produced by refluxing a compound of formula II with an excess of a compound of formula III.

If compound III is a compound R—CH$_2$—L, L can be any easily displaced group, such as halo, p-toluene sulfonyloxy, methyl sulfonyloxy, trifluoromethylsulfonyloxy and the like.

Compounds of general formula II may be prepared by cleaving the group COOR$^a$ from the corresponding carbamates IV, for example, via acid hydrolysis (e.g., HCl) or base hydrolysis (e.g., KOH):

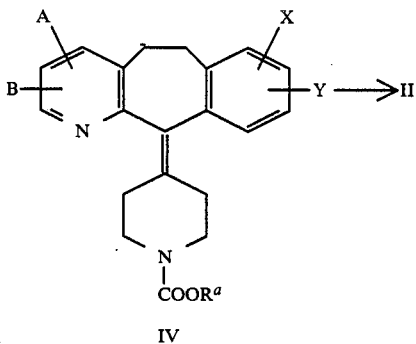

IV wherein R$^a$ is a group which does not prevent the cleavage reaction, e.g., R$^a$ is alkyl such as ethyl.

Alternatively, depending upon the nature of R$^a$, as determined by one skilled in the art, Compound IV may be treated with an organometallic reagent (e.g., CH$_3$Li), a reductive reagent (e.g., Zn in acid), etc., to form compounds of formula II.

Compound IV may be prepared from the N-alkyl compound shown as formula V below, in the manner disclosed in U.S. Pat. Nos. 4,282,233 and 4,335,036, the teachings of which are incorporated herein by reference.

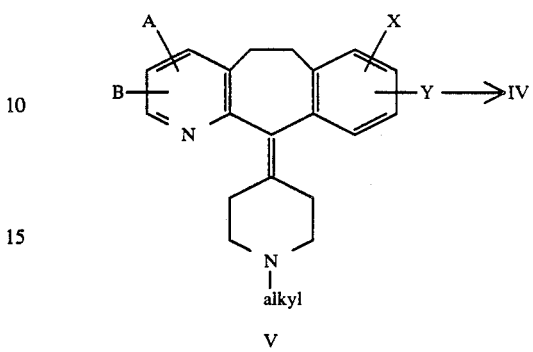

V

Compounds of structural formula V may be produced methods disclosed generally in U.S. Pat. No. 3,326,924, the teachings of which are incorporated herein by reference.

Compounds of formula V may alternatively be prepared by a ring closure reaction, wherein the desired cycloheptene ring is formed by treating compound VI with a super acid having a Hammett acidity function of less than minus 12, e.g., minus 13, minus 14, etc. This measure of acidity is defined in Hammett, Louis P., and Deyup, Alden J., *Journal of the American Chemical Society*, Vol. 54, 1932, p. 2721. Suitable super acids for this purpose include, for example, HF/BF$_3$, CF$_3$SO$_3$H (triflic acid), CH$_3$SO$_3$H/BF$_3$, etc. The reaction can be performed in the absence of or with an inert co-solvent such as CH$_2$Cl$_2$. The temperature and time of the reaction vary with the acid employed. For example, with HF/BF$_3$ as the super acid system the temperature may be controlled so as to minimize side reactions, such as HF addition to the exocyclic double bond. For this purpose, the temperature is generally in the range of from about +5° C. to −50° C., preferably from about −30° C. to −35° C. With CF$_3$SO$_3$H as the super acid system, the reaction may be run at elevated temperatures, e.g., from about 25° C. to about 150° C. and at lower temperatures but the reaction then takes longer to complete.

Generally the super acid is employed in excess, preferably in amounts of from about 1.5 to about 30 equivalents. For example, with HF/BF$_3$ as the super acid system the molar ratio of HF to the compound of formula VI in the reaction mixture is preferably from about 30 to about 1.5, more preferably 2.5 to 1.5. In such system, the molar ratio of BF$_3$ to the compound of formula VI in the reaction mixture is preferably from about 15 to about 0.75, more preferably from about 1 to about 0.75.

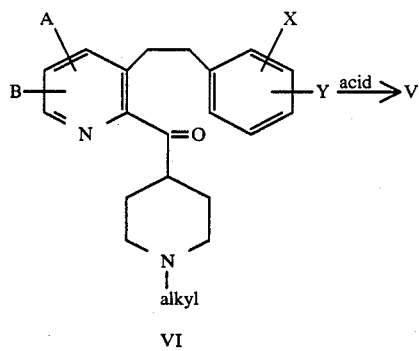

VI

A ketone compound of formula VI may be formed by hydrolysis of VII e.g., such as by reacting a Grignard intermediate of formula VII with an aqueous acid (e.g., aqueous HCl). $I^a$ in formula VII represents chloro, bromo or iodo.

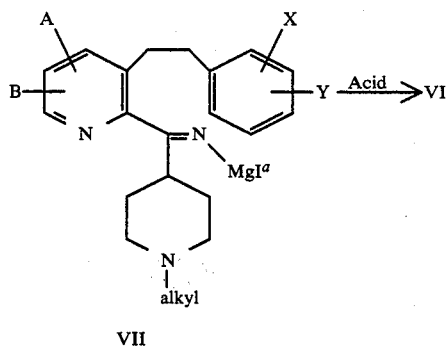

VII

The Grignard intermediate VII is formed by the reaction of the cyano compound VIII with an appropriate Grignard reagent IX prepared from 1-alkyl-4-halopiperidine. The reaction is generally performed in an inert solvent, such as ether, toluene, or tetrahydrofuran, under general Grignard conditions e.g., temperature of from about 0° C. to about 75° C.

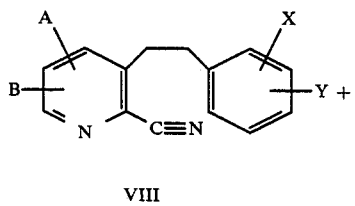

VIII

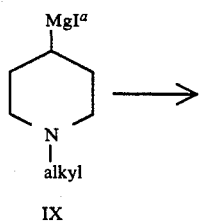

IX

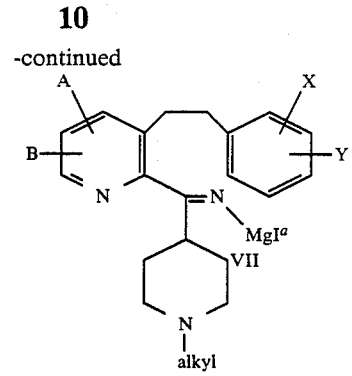

The cyano compound of formula VIII is produced by converting a tertiary butyl amide of formula X with a suitable dehydrating agent, such as $POCl_3$, $SOCl_2$, $P_2O_5$, toluene sulfonyl chloride in pyridine, oxalyl chloride in pyridine, etc. This reaction can be performed in the absence of or with a co-solvent, such as xylene. The dehydrating agent such as $POCl_3$ is employed in equivalent amounts or greater and preferably in amounts of from about 2 to about 15 equivalents. Any suitable temperature and time can be employed for performing the reaction, but generally heat is added to accelerate the reaction. Preferably the reaction is performed at or near reflux.

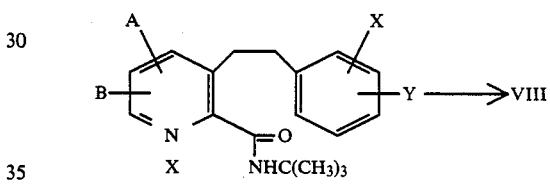

The tert-butylamide of formula X may be produced by reaction of a compound of formula XI, in the presence of base, where G is chloro, bromo or iodo.

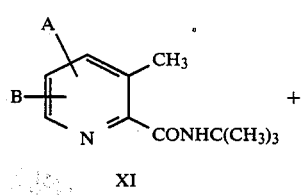

XI

+

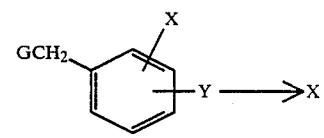

The compound of formula XI may be formed by a Ritter reaction, wherein 2-cyano-3-methylpyridine is reacted with a tertiary butyl compound in acid, such as concentrated sulfuric acid or concentrated sulfuric acid in glacial acetic acid. Suitable tertiary butyl compounds include, but are not limited to, t-butyl alcohol, t-butyl chloride, t-butyl bromide, t-butyl iodide, isobutylene or any other compound which under hydroltyic conditions forms t-butyl carboxamides with cyano compounds. The temperature of the reaction will vary depending upon the reactants, but generally the reaction is conducted in the range of from about 50° C. to about 100° C. with t-butyl alcohol. The reaction may be performed with inert solvents, but is usually run neat.

B. The compounds of formula I may be made by an alternative process using direct conversion of the N-alkyl compound V with an appropriate compound of formula III such as an acyl halide or acyl anhydride. Preferably the reaction is run in the presence of an appropriate nucleophile (e.g. LiI, etc.) and solvent (e.g., toluene, dioxane or xylenes). An appropriate base, may be added, and heating may be required. Typically, a temperature ranging from 50°–150° C. (preferably 100°–120° C.) is desired.

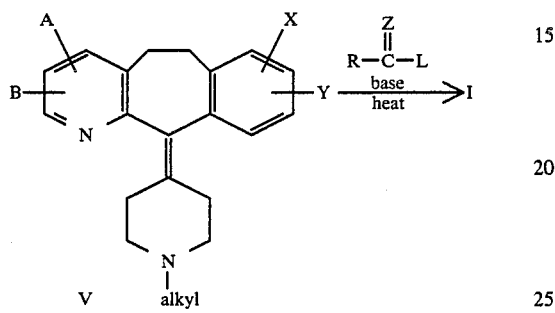

Compound V is prepared as described in part A above.

C. A second alternative process for the formation of compounds having general structural formula I involves direct cyclization of the Compound XII as shown below.

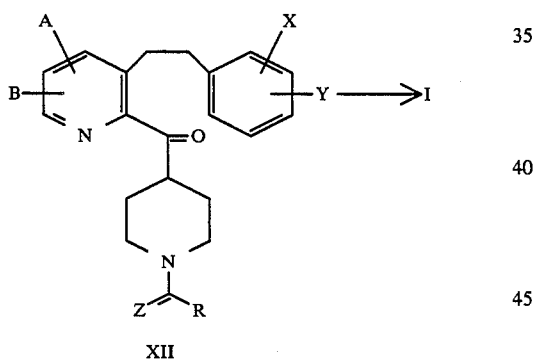

Cyclization to form the cycloheptene ring is accomplished with a strong acid (e.g., triflic, polyphosphoric acid, HF/BF$_3$), and may be performed in an inert solvent, such as ether, toluene or THF. The super acid may have a Hammett acidity function of less than about minus 12; e.g., minus 13, minus 14, etc. to produce a compound of formula I. The temperature and time may vary with the acid employed, as described in process B above.

Compounds of formula XII where Z=O or S may be prepared by treating a compound of formula VI with an appropriate acyl halide or acyl anhydride of formula III. Most preferably this reaction is run in the presence of a good nucleophile, such as LiI, in the appropriate solvent, such as toluene, dioxane or xylene, and at a temperature ranging from 50°–150° C., preferably 100°–120° C.

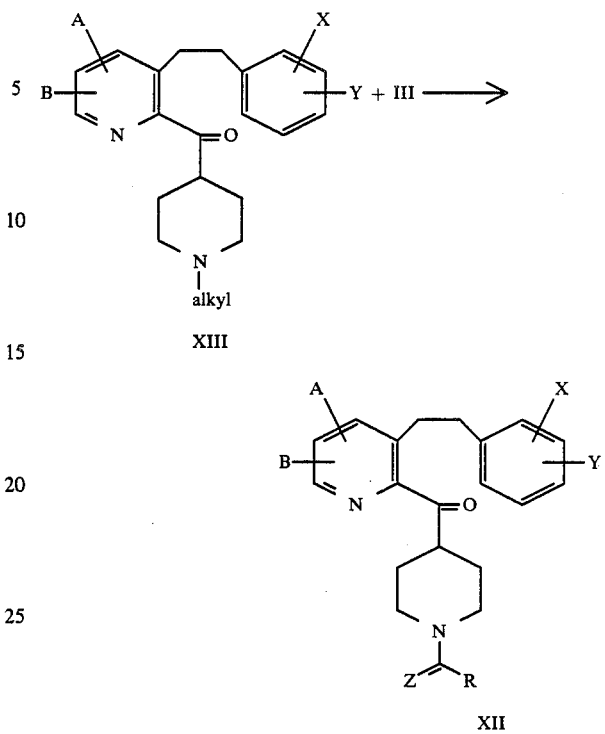

A second method of preparing compounds of formula XII involves reacting an unsubstituted piperidylidene compound of formula XIV with the appropriate acyl halide or acyl anhydride of formula III in the presence of base, such as pyridine or triethylamine. Alternatively, if L=OH of compound III, then coupling of compound XIV with compound III may require use of a conventional coupling reagent, such as DCC or CDI. If compound III is of the formula RCH$_2$L, compounds of formula I where Z=H2 will be produced. In such case, the leaving group can be any easily displaced group, such as halo, p-toluene sulfonyloxy, methyl sulfonyloxy, trifluoromethyl sulfonyloxy, etc.

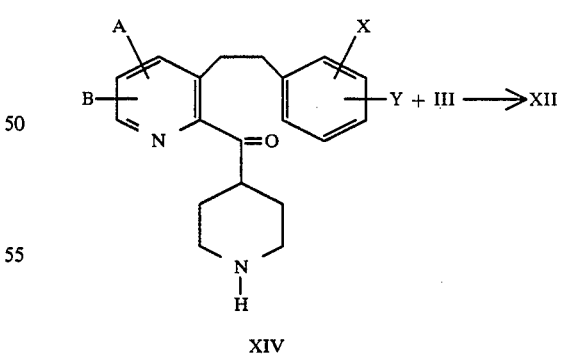

Compounds of formula XIV are produced from the corresponding carbamates of formula XV, via acid, such as aqueous hydrochloric acid, or base, such as potassium hydroxide, hydrolysis. Alternatively, some compounds can be prepared by treating the carbamate, formula XV, with an organometallic reagent, such as methyl lithium, a reductive reagent, such as zinc in acid, etc., depending upon the nature of the R$^c$ group. For example, if $R^c$ is a simple alkyl group, $CO_2R^c$ may be cleaved by alkaline hydrolysis at 100° C.

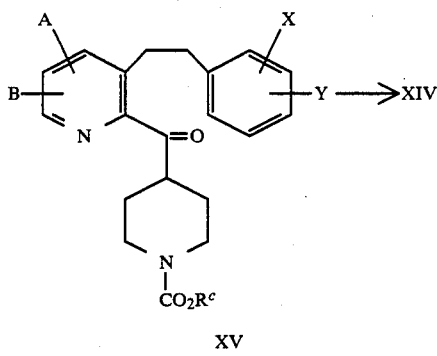

XV

The carbamate compounds of formula XV may be prepared from the appropriate alkyl compound of formula VI by treatment with a chloroformate preferably in an inert solvent, such as toluene with warming to approximately 80° C.

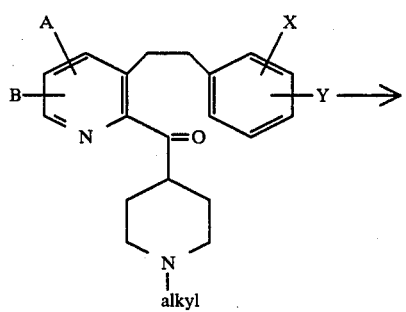

VI

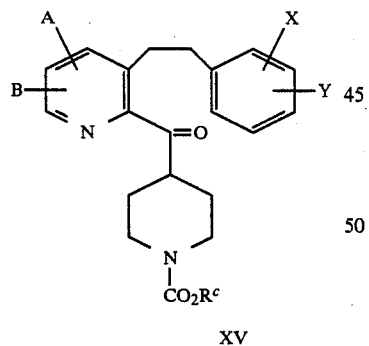

XV

Compund of formula VI may be prepared as described in process A above.

To make a compound of formula I where Z represents sulfur, a compound of formula I where Z is oxygen is reacted with $P_2S_5$ or Lawesson's reagent, or another reagent capable of introducing sulfur in place of oxygen.

The reaction may take place at elevated temperature in pyridine, toluene or other suitable solvents. Lawesson's reagent has the formula

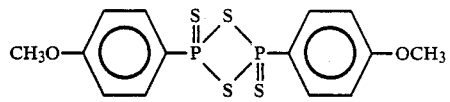

In this and other reactions, numerous conversions of a compound of formula I (Z=O) to another compound of formula I (Z=S) are possible.

In the above processes A–C, it is sometimes desirable and/or necessary to protect certain A, B, X, Y, Z, etc., groups during the reactions. Conventional protecting groups are operable. For example, the groups listed in column 1 of the following table may be protected as indicated in column 2 of the table:

| 1. Group to be Protected | 2. Protected Group |
| --- | --- |
| —COOH | —COOalkyl, —COObenzyl, —COOphenyl |
| \>NH | \>N—CO₂alkyl, \>N—CO₂benzyl, \>N—CO₂CH₂CCl₃ |
| \>CO | (cyclic ketal) |
| —OH | —O—(tetrahydropyranyl), —O—CH₃ |
| —NH₂ | —N(succinimide) |

Of course, other protecting groups well known in the art may be used. After the reaction or reactions, the protecting groups may be removed by standard procedures.

The compounds of the invention possess platelet-activating factor ("PAF") antagonistic properties. The compounds of the invention are therefore useful whenever PAF is a factor in the disease or disorder. This includes allergic diseases such as asthma, adult respiratory distress syndrome, urticaria and inflammatory diseases such as rheumatoid arthritis and osteoarthritis. For example, PAF is an important mediator of such processes as platelet aggregation, smooth muscle contraction (especially in lung tissue), vascular permeability and neutrophil activation. Recent evidence implicates PAF as an underlying factor involved in airway hyperreactivity.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

PAF Antagonism Assay

A. In vitro Assay:

Preparation of platelet-rich plasma (PRP): Human blood (50 ml) was collected from healthy male donors in an anticoagulant solution (5 ml) containing sodium citrate (3.8%) and dextrose (2%). Blood was centrifuged at 110×g for 15 min. and the supernatant (PRP) carefully transferred into a polypropylene tube. Platelet-poor-plasma (PPP) was prepared by centrifuging PRP at 12,000×g for 2 min. (Beckman Microfuge B). PRP was used within 3 hours of drawing the blood.

Platelet Aggregation Assay: When an aggregating agent such as PAF is added to PRP, platelets aggregate. An aggregometer quantifies this aggregation by measuring light (infra-red) transmission through PRP and comparing to PPP. The aggregation assays were performed using a dual-channel aggregometer (Model 440, Chrono-Log Corp., Havertown, PA). PRP (0.45 ml) in aggregometer curettes was continually stirred (37° C.). Solutions of test compounds or vehicle were added to the PRP, and after incubation for 2 min., 10–15 $\mu$l aliquots of PAF solution were added so as to achieve a final concentration of $1-5\times10^{-8}$M. Incubations were continued until the increase in light transmission reached a maximum (usually 2 min). Values for inhibition were calculated by comparing maximal aggregation obtained in the absence and the presence of the compound. For each experiment, a standard PAF antagonist such as alprazolam was used as a positive internal control. The inhibitory concentration ($IC_{50}$) is the concentration of compound in micromoles at which 50% of the aggregation is inhibited, as measured by the light transmission through each sample of PRP as compared to PPP. The test results are shown below in Table A.

PAF is also a known bronchoconstrictive agent in mammals. Hence, PAF antagonism can be evaluated by measuring inhibition by the compounds of the invention in PAF-induced bronchoconstriction in guinea pigs.

PAF-Induced Bronchospasm in Guinea Pigs

B. In Vivo Assay

Non-sensitized guinea pigs were fasted overnight, and the following morning were anesthetized with 0.9 ml/kg i.p. of dialurethane (0.1 g/ml of diallybarbituric acid, 0.4 g/ml of ethylurea and 0.4 g/ml of urethane). The trachea was cannulated and the animals were ventilated by a Harvard rodent respirator at 55 strokes/min. with a stroke volume of 4 ml. A side arm to the tracheal cannula was connected to a Harvard pressure transducer to obtain a continuous measure of intratracheal pressure, which was recorded on a Harvard polygraph. The jugular vein was cannulated for the administration of compounds. The animals were challenged i.v. with PAF (0.4 ug/kg in isotonic saline containing 0.25% BSA) and the peak increase in inflation pressure that occurred with 5 min. after challenge was recorded. Test compounds were administered either orally (2 hrs. prior to PAF as a suspension in 0.4% methylcellulose vehicle) or intravenously (10 min. prior to PAF as a solution in dimethylsulfoxide).

The compound 8-chloro-11-(1-acetyl-4-piperidylidene)-6,11-dihydro-5H-benzo[5,6]cyclohepta[1,2-b]pyridine at a dose of 1 mg/kg given intravenously inhibited PAF-induced bronchospasm by 75% as measured by this procedure. Similarly, the compound 8-fluoro-11-(1-acetyl-4-piperidylidene)-6,11-dihydro-5Hbenzo[5,6]cyclohepta[1,2-b]pyridine when administered at 3 mg/kg (iv) inhibited PAF-induced bronchospasm by 99%. The compound 9-fluoro-11-(1-acetyl-4-piperidylidene)6,11-dihydro-5H-benzo[5,6]cyclopheta[1,2-b]pyridine when administered at 3 mg/kg (iv) inhibited PAF-induced bronchospasm by 97%.

The compounds of the invention also possess antihistaminic properties which may be assessed by test procedure C below. Test procedure C, "Prevention of histaminic-induced lethality" demonstrates basic antihistaminic activity of representative compounds of structural formula I. Greater protection against histamine lethality is indicative of strong antihistaminic properties.

Test procedures D, E and F demonstrate the extent of CNS activity induced by the compounds of the invention. The presence of strong CNS activity indicates a high probability of sedation caused by the compounds, a typically undesirable side effect of antihistamines. Consequently, a low level of CNS activity is preferred in most circumstances.

Antihistamine Activity Assay

C. Prevention of histamine-induced lethality in guinea pigs. The compounds shown below in Table A were evaluated for antihistamine activity by their ability to protect female albino guinea pigs (250–350 g) against death induced by the intravenous injection of histamine dihydrochloride at 1.1 mg/kg, which is approximately twice the $LD_{99}$. Doses of the antagonists were administered orally to separate groups of fasted animals 1 hour prior to the challenge with histamine and protection from death recorded for 30 minutes after histamine. $ED_{50}$ values were determined for each drug by probit analysis.

CNS Activity assays

D. Antagonism of Physostigmine Lethality. The physostigmine-induced lethality test is indicative of CNS activity and the test described is a modification of the technique reported by COLLIER et al., *Br. J. Pharmac.*, 32, 295–310 (1968). Physostigmine salicylate (1.0 mg/kg s.c.) produces 100% lethality when administered to mice grouped 10 per plastic cage (11×26×13 cm). Test agents were administered orally 30 minutes prior to physostigmine. The number of survivors were counted 20 minutes after physostigmine administration.

E. Antagonism of Acetic Acid Writhing. The acetic acid writhing test is a second test useful for determining CNS activity, and is essentially that described by HENDERSHOT and FORSAITH, *J. Pharmac. Exp. Ther.*, 125, 237–240 (1959), except that acetic acid rather than phenylquinone was used to elicit writhing. Mice were injected with 0.6% aqueous acetic acid at 10 mg/kg i.p. 15 minutes after oral administration of the test drug. The number of writhes for each animal was counted during a 10 minute period starting 3 minutes after acetic acid treatment. A writhe was defined as a sequence of arching of the back, pelvic rotation and hind limb extension.

F. Antagonism of Electro-Convulsive Shock (ECS). The ECS test is a third test useful for determining CNS activity. For the ECS test, a modification of the method of TOMAN et al., *J. Neurophysiol.*, 9, 231–239 (1946), was used. One hour after oral administration of the test drug or vehicle, mice were administered a 13 mA, 60 cycle a.c. electroconvulsant shock (ECS) for 0.2 seconds via corneal electrodes. This shock intensity produces tonic convulsions, defined as extension of the hind limbs, in at least 95% of vehicle-treated mice.

Of the above test procedures for measuring CNS activity, the physostigmine-induced lethality test is believed to be a major index of non-sedating characteristics, since it reflects mainly central anticholinergic potency which is believed to contribute to sedative activity.

Representative results of these test procedures with compounds of the invention are presented below in Table A.

ity are required, a different compound of the invention would be utilized by the clinician.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets may be comprised

TABLE A

Compound

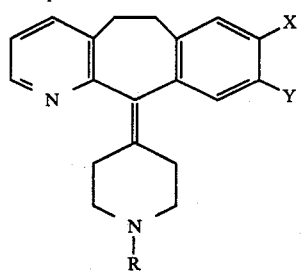

| | Antihistaminic Activity Guinea pig oral dose | | CNS Activity | | | PAF Antagonism (in vitro) | |
|---|---|---|---|---|---|---|---|
| | | | Physostigmine lethality $ED_{50}$ | Acetic writhing $ED_{50}$ | ECS test $ED_{50}$ | Dose | % PAF |
| | (mg/kg) Dose | % Survival | (mg/kg) | (mg/kg) | (mg/kg) | (micromoles) | Antagonism |
| R = COCH$_2$CH$_3$ X = Cl | 5 PO 1 PO | 80 40 | >320 | >320 | >320 | 3 | 60 |
| R = —COCH$_2$OCH$_3$ X = F Y = H | 5 PO 1 PO | 100 100 | >320 | >320 | >320 | 10 | 9 |
| R = —COCH$_3$ X = F Y = H | 5 PO | 20 | * | * | * | 0.7 | 50 |
| R = —COCH$_3$ X = H Y = F | 5 PO | 0[1] | * | * | * | 0.9 | 50 |
| R = —CH$_3$** X = H Y = H | $ED_{50}$ = 0.009 | | 6.1 | 8.9 | >80 | >100 | 50 |
| R = —CO$_2$C$_2$H$_5$** X = Cl Y = H | $ED_{50}$ = 0.19 | | >320 | >320 | >320 | 175 | 50 |
| R = —CSPh X = Cl Y = H | 5 PO 1 PO | 60 0 | >320 | >320 | >320 | * | * |
| R = —COCH$_3$ X = Cl Y = H | 5 PO 1 PO | 100 60 | >320 | >160 | >320 | 0.7 | 50 |
| R = —COPh X = CL Y = H | 5 PO 1 PO | 100 0 | * | * | * | 10 | 9 |
| R = —COCH$_2$OCH$_3$ X = Cl Y = H | 5 PO 1 PO | 80 80 | >320 | >320 | >320 | 6 | 50 |
| R = —COCH$_2$CH$_2$CH$_3$ X = Cl Y = H | 5 PO 1 PO | 100 40 | >320 | >320 | >320 | * | * |
| R = —COSCH$_2$CH$_3$ X = Cl Y = H | 5 PO 1 PO | 80 100 | >320 | >320 | >320 | 10 | 0 |

*Not tested
**Standard known antihistamine.
[1]Expected to have some activity at a higher dose.

As seen from the data of Table A and from the PAF induced bronchospasm inhibition test results, the compounds of structural formula I exhibit PAF antagonist and antihistaminic properties to varying degrees, i.e., certain compounds have strong PAF antagonistic activity, but have weaker antihistaminic activity. Other compounds are strong antihistamines but weaker PAF antagonists. Several of the compounds are both strong PAF antagonists and potent antihistamines. Consequently, it is within the scope of this invention to use each of these compounds when clinically appropriate. For example, if a strong PAF antagonist is required, but weaker antihistaminic activity is necessary, such a compound could be chosen by the clinician. Alternatively, if both potent PAF antagonism and antihistaminic activof from about 5 to about 70 percent active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in polyethylene glycol and/or polypropylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxy-methylcellulose and other well-known suspending agents.

Liquid form preparations may also include solutions for intranasal administration.

Aerosol preparations suitable for inhalation may include solutions and solids in powder form, which may be in combination with a pharmaceutically acceptable carrier, such as an inert compressed gas. Inhalation aerosols may be packaged in a pressure resistant container, which may have a metered dose feature suitable for administration into the oral cavity for inhalation, or into the nasal passageways, thereby delivering a precise amount of aerosol per use.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component, e.g., an effective amount to achieve the desired purpose. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these packaged form. The compositions can, if desired, also contain other therapeutic agents.

The quantity of active compound in a unit dose of preparation may be varied or adjusted from about 0.1 mg to 1000 mg, more preferably from about 1 mg. to 100 mg, according to the particular application. The appropriate dosage can be determined by comparing the activity of the compound with the activity of a known antihistaminic compound such as 8-chloro-6,11-dihydro-11-(1-ethoxycarbonyl-4-piperidylidene)-5H-benzo[5,6]cyclohepta[1,2-b]pyridine, which compound is disclosed in U.S. Pat. No. 4,282,233.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgement of the attending clinician considering such factors as age, condition and size of the patient as well as severity of the symptom being treated. A typical recommended dosage regimen is oral administration of from 0.25 to 100 mg/day, preferably 10 to 20 mg/day, in two to four divided doses to achieve relief of the symptoms.

The following examples are intended to illustrate, but not to limit, the present invention. Preparative Example 1A through G follows the reaction sequence shown below.

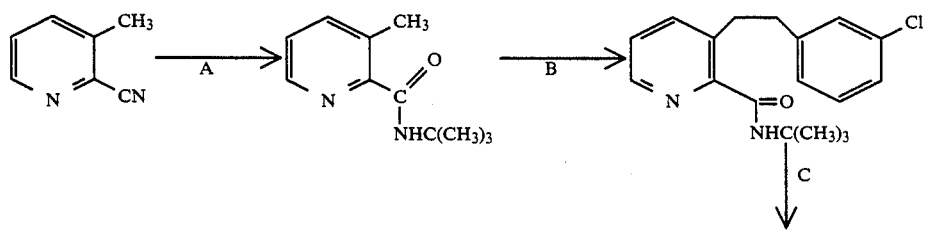

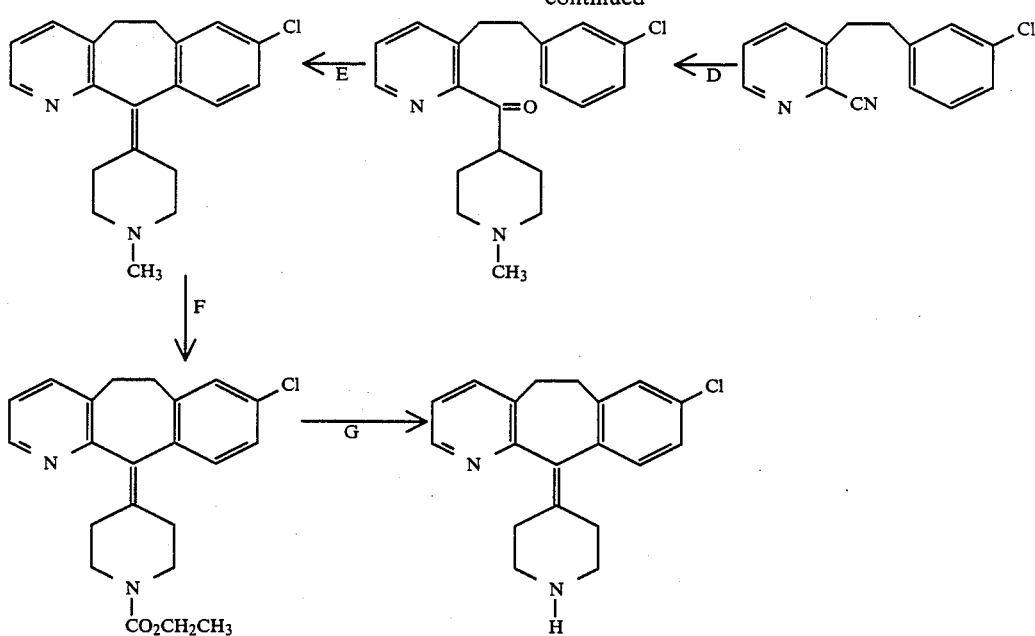

PREPARATIVE EXAMPLE I

A. N-(1,1-DIMETHYLETHYL)-3-METHYL-2-PYRIDINE CARBOXAMIDE

Suspend 2-cyano-3-methyl pyridine (400 g) in t-butanol (800 mL) and heat to 70° C. Add concentrated sulphuric acid (400 mL) dropwise over 45 minutes. Maintain the temperature at 75° C., until the reaction is complete, and for an additional 30 minutes. Dilute the mixture with water (400 mL), charge with toluene (600 mL) and bring to pH 10 with concentrated aqueous ammonia. Maintain the temperature at 50°–55° C. during the work up. Separate the toluene phase, and reextract the aqueous layer. Combine toluene phases and wash with water. Remove the toluene to yield the title compound N-(1,1-dimethylethyl)-3-methyl-2-pyridine carboxamide, as an oil, from which solid product is crystallized. (Yield 97%, as determined by an internal standard assay with gas chromatography).

B. 3-[2-(3-CHLOROPHENYL)ETHYL]-N-(1,1-DIMETHYLETHYL)PYRIDINE CARBOXAMIDE

Dissolve the title compound of Preparative Example 1A, N-(1,1-dimethylethyl)-3-methyl-2-pyridine carboxamide (31.5 g.) in tetrahydrofuran (600 mL) and cool the resulting solution to −40° C. Add n-butyllithium (2 eg.) in hexane while maintaining the temperature at −40° C. The solution turns deep purple-red. Add sodium bromide (1.6 g) and stir the mixture. Add solution of m-chlorobenzylchloride (26.5 g., 0.174 mole) in tetrahydrofuran (125 mL) while maintaining the temperature at −40° C. Stir the reaction mixture until the reaction is complete as determined by thin layer chromatography. Add water to the reaction until the color is dissipated. Extract the reaction mixture with ethyl acetate, wash with water, and concentrate to a residue which is the title compound. (Yield 92% as shown by chromatography).

C. 3-[2-(3-CHLOROPHENYL)ETHYL]-2-PYRIDINE-CARBONITRILE

Heat a solution of the title compound of Preparative Example 1B, 3-[2-(3-chlorophenyl)ethyl]-N-(1,1-dimethylethyl)-2-pyridine carboxamide (175 g, 0.554 mole) in phosphorous oxychloride (525 mL, 863 g, 5.63 mole) and reflux for 3 hours. Determine completion of the reaction by thin layer chromatography. Remove any excess phosphorous oxychloride by distillation at reduced pressure and quench the reaction in a mixture of water and isopropanol. Bring to pH 5–7 by adding 50% aqueous sodium hydroxide solution while maintaining the temperature below 30° C. Filter the crystalline slurry of crude product and wash with water. Purify the crude product by slurrying the wet cake in hot isopropanol, and cool to 0°–5° C. Filter the product, wash with hexane and dry at a temperature below 50° C. to yield the title compound. (Yield: 118g (HPLC purity 95.7%), m.p. 72° C.–73° C, 89.4% of theory).

D. 1-(METHYL-4-PIPERIDINYL)[3-(2-(3-CHLOROPHENYL)ETHYL)-2-PYRIDINYL]METHANONE HYDROCHLORIDE

Dissolve the title compound of Preparative Example 1C, (118 g, 0.487 mole) in dry tetrahydrofuran (1.2 L) and add N-methyl-piperidyl magnesium chloride (395 mL, 2.48 mole/liter, 0.585 mole, 1.2 eq.) over 15 minutes. Maintain the temperature at 40° C.–50° C. by cooling with water as necessary, for 30 minutes. Determine completion of the reaction by thin-layer chromatography. Quench the reaction by reducing the pH to below 2 with 2N HCl and stir the resulting solution at 25° C. for 1 hour. Remove the bulk of the tetrahydrofuran by distillation and adjust the resulting solution to pH 3.5 by addition of aqueous sodium hydroxide. Cool to 0° to 5° C. and filter off the crystalline hydrochloride salt product. Wash with ice cold water and dry to constant weight at 60° C. to yield the title compound. (Yield: 168.2 g (HPLC purity 94%), m.p. 183°–185° C., 89% of theory).

E: 8-CHLORO-6,11-DIHYDRO-11-(1-METHYL-4-PIPERIDYLIDENE)-5H-BENZO[5,6]CYCLOHEPTA[1,2-b]PYRIDINE

Dissolve the title compound of Preparative Example 1D above (59 g, 0.15 mole) in hydrofluoric acid (120 mL, 120 g, 6.0 mole) at −35° C. and add boron trifluoridine (44.3 g, 0.66 mole) over 1 hour. Determine completeness of the reaction by thin-layer chromatography. Quench the reaction using ice, water and potassium hydroxide bringing the solution to a final pH of 10. Extract the product with toluene and wash with water and brine. Concentrate the toluene solution to a residue, and dissolve in hot hexane. Remove the insolubles by filtration and concentrate the filtrate to yield the title compound as an off-white powder. (Yield: 45.7 g (HPLC purity: 95%), 92% of theory).

Alternative Step E: 8-CHLORO-6,11-DIHYDRO-11-(1-METHYL-4-PIPERIDYLIDENE)-5H-BENZO[5,6]CYCLOHEPTA[1,2-b]-PYRIDINE React the title compound of Preparative Example 1D above (177 g, 0.49 mole) in trifluoromethanesulfonic acid (480 ml, 814.1 g, 5.31 mole) at 90°–95° C. for 18 hours under nitrogen. Determine the completeness of the reaction by thin-layer chromatography. Cool the reaction and quench the reaction with ice-water and adjust the pH to 6 with barium carbonate. Extract the product with methylene chloride, and concentrate under reduced pressure to about 1 liter. Wash with water, and extract the product into 1 N HCl which is treated with 30 g of Darco, and filter through celite. Adjust the pH of the filtrate to 10 with aqueous sodium hydroxide (50%), extract the product into methylene chloride, and remove under reduced pressure to form a residue. Dissolve the residue in hot hexane, and filter to remove insolubles. Concentrate the filtrate to yield the title compound as a beige powder. (Yield: 126 g (HPLC purity 80%), 65% of theory).

F. 8-CHLORO-6,11-DIHYDRO-11-(1-ETHOXYCARBONYL-4-PIPERIDYLIDENE)-5H-BENZO[5,6]CYCLOHEPTA[1,2'-b]PYRIDINE

Dissolve the title compound of Preparative Example 1E above (45.6 g, 0.141 mole) in toluene (320 mL) at 80° C. and to it gradually add ethyl chloroformate (40.4 mL, 45.9 g, 0.423 mole). Following complete addition, maintain the temperature at 80° C. for 1 hour, then add diisopropylethylamine (2.7 mL, 2.00 g, 0.016 mole) and additional ethyl chloroformate (4.1 mL, 4.65 g, 0.0429 mole). Monitor completeness of the reaction by thin layer chromatography. Upon completion, cool the reaction mixture to ambient temperature, and wash the toluene solution with water. Concentrate the organic layer to a residue and dissolve in hot acetonitrile (320 mL). Decolorize the solution with 14 g of Darco. Remove the Darco by filtration and concentrate the filtrate to a crystalline slurry. Cool the mixture to 0°–5° C., and isolate the product by filtration. Wash with cold acetonitrile and dry the product at below 70° C. to yield the title compound. (Yield: 42.4 g (HPLC purity 97.4%), 80% of theory).

G. 8-CHLORO-11-(4-PIPERIDYLIDENE)-6,11-DIHYDRO-5H-BENZO[5,6]CYCLOHEPTA[1,2-b]PYRIDINE

Hydrolize the title compound of Preparative Example 1E, 8-chloro-6,11-dihydro-11-(1-methyl-4-piperidylidene)-5H-benzo[5,6]cyclohepta[1,2-b]pyridine (39 g, 0.101 mole) with KOH (50 g) in ethanol (305 mL) and water (270 mL) at reflux under an argon atmosphere for 64 hours. Partially distill off the ethanol and dilute the residue with brine, and extract with ethylacetate (3×). Wash the combined organic phases with water and dry with $Na_2SO_4$. Remove the solvent to give a solid which can be recrystallized from toluene to give the title compound as a white solid. (Yield: 24.5 g, 77%, melting point 154°–155° C.).

By substituting in step 1B above, an appropriately substituted benzylhalide listed in Table 1 below for meta-chlorobenzylchloride, and employing basically the same methods as steps C through G, the products listed in Table 1 are prepared by the process of Preparative Example 1 above. Reaction times are determined by TLC or HPLC. In some instances purification of the product by chromatography is necessary.

TABLE I

Product of step G

| Benzyl halide | Product | Melting Point |
|---|---|---|
| BrCH₂—C₆H₄—F (meta) | X = F, Y = H | 133.5–134.5° C.[a] |
| ClCH₂—C₆H₃—Cl,Cl | X = Cl, Y = Cl | 150–152° C.[b] |

TABLE I-continued
Product of step G
| Benzyl halide | | Product Melting Point |
|---|---|---|
| BrCH₂—C₆H₄—CH₃ | X = CH₃, Y = H | 142–144° C.[c] |
[a]Step E requires trifluromethanesulfonic acid.
[b]Recrystallized from toluene.
[c]Recrystallized from acetone and pentane.
Preparative Example 2A through 2G follows the reaction sequence shown below.
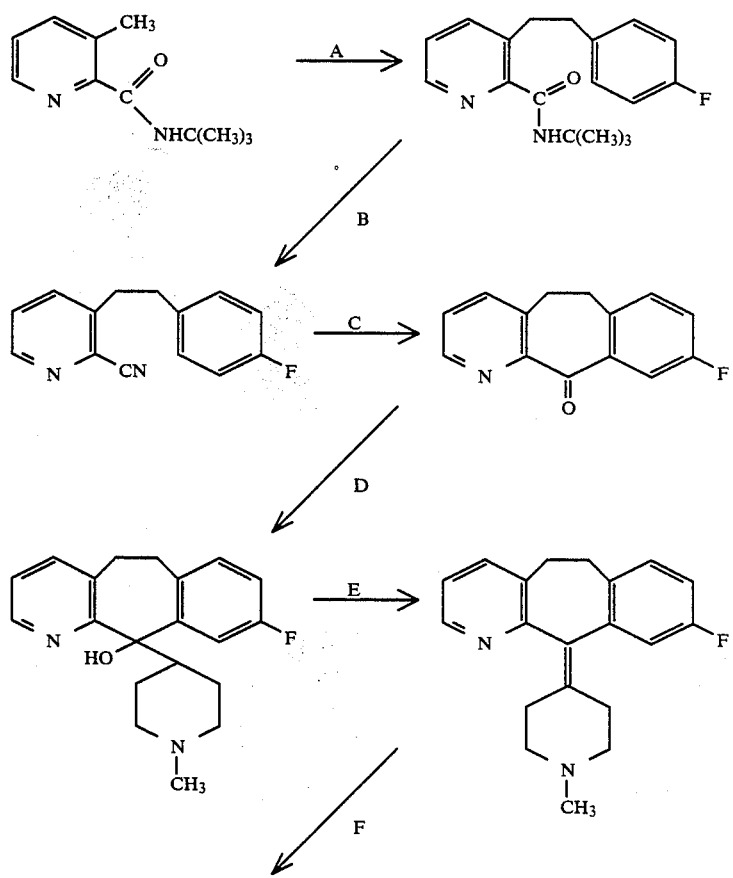

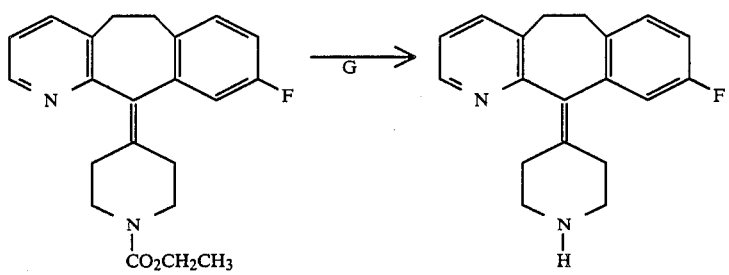

PREPARATIVE EXAMPLE 2

PREPARATION OF 9-FLUORO-11-(4-PIPERIDYLIDENE)-6,11-DIHYDRO-5H-BENZO[5,6]CYCLOHEPTA[1,2-b]PYRIDINE

A. N-(1,1-DIMETHYLETHYL)-3-[2-(4-FLUOROPHENYL)ETHYL]-2-PYRIDINE CARBOXAMIDE

Cool a solution of N-(1,1-dimethylethyl)-3-methyl-2-pyridinecarboxamide (38.4 g, 0.2 mole) in dry THF (250 mL) to $-40°$ C. and add n-butyl lithium (185 mL, 0.44 mole). Add sodium bromide (1.9 g, 18 mmol.) and stir for 15 minutes. Add 4-fluorobenzylchloride (31.8 g. 0.22 mole) and stir for 2.5 hours while warming to $-5°$ C. Quench the reaction with water and extract the product twice with ethyl acetate, then wash with brine (2×). Dry the organic phase over $Na_2SO_4$, filter and remove the solvent to give the title compound. (60.0 g, Yield 99%, m.p. 59°–61° C.)

B. 3-[2-(4-FLUOROPHENYL)ETHYL]-2-PYRIDINE-CARBONITRILE

Heat the title compound of Preparative Example 2A above (60.0 g, 0.2 mole) in $POCl_3$ (200 mL) to 110° C. under an argon atmosphere for 3.5 hours. Pour the reaction mixture onto ice and basify with NaOH (50%) solution. Extract the mixture with ethyl acetate (3x) and wash with water. Wash with brine and dry over $Na_2SO_4$. Remove the solvent and pass the residue through a coarse $SiO_2$ (60–200 mesh) column to give the title compound as a white solid (40 g, Yield 88%, m.p. 48°–49° C.).

C. 9-FLUORO-5,6-DIHYDRO-(1H)-BENZO[5,6-]CYCLOHEPTA[1,2-b]-PYRIDIN-11-ONE

Cyclize the title compound of Preparative Example 2B above (31.5 g, 139 mmol) in polyphosphoric acid (1.24 kg) at 200° C. for 5.5 hours. Pour onto ice and basify with NaOH solution (50%). Extract the product with chloroform (3x) and wash with brine. Dry the organic phase with $Na_2SO_4$, filter and remove the solvent to give the title compound (20.4 g, yield 64%, m.p. 78°–81° C. after recrystallization from diisopropyl ether).

D. 9-FLUORO-6,11-DIHYDRO-11-(1-METHYL-4-PIPERIDINYL)-5H-BENZO[5,6]CYCLOHEPETA[1,2-b]PYRIDIN-11-OL

Dissolve the title compound of Preparative Example 2C above (10.0 g, 44 mmol) in THF (100 mL) and add slowly to a cooled ($-40°$ C.) solution of the Grignard reagent prepared from N-methyl-4-chloropiperidine (57.9 mL, 88 mmol) in THF (70 mL). Stir the mixture for about 1 hour while warming up to 0° C. Quench the reaction with $NH_4Cl$ solution and extract with ethyl acetate (2×). Wash the organic phase with brine and dry over $Na_2SO_4$, filter and remove the solvent. Purify the residue with flash chromatography and elute with methanol (5%) in $CHCl_3$ to give the title compound as white granular crystals. (10.1 g, Yield 70%, m.p. 126°–127° C. after recrystallization from diisopropyl ether.)

E. 9-FLUORO-11-(1-METHYL-4-PIPERIDYLENE)-6,11-DIHYDRO-5H-BENZO[5,6-]CYCLOHEPTA[1,2-b]PYRIDINE

Add the title compound of Preparative Example 2D above (7.3 g, 22.3 mmol) to a mixture of cooled $H_2SO_4$ and $CF_3SO_3H$ (1:1), 146 mL). Stir the reaction mixture for 0.5 hours at ice bath temperature and then at room temperature for 1.5 hours. Pour the reaction mixture onto ice and basify with NaOH (50%) solution. Extract the product with ethyl acetate (3×) and wash with brine.

Dry the organic phase over $Na_2SO_4$, filter and remove the solvent to give a crude oil. Charcoal the oil and recrystallize from ethyl acetate and isopropyl ether to give the title compound. (5.6 g, Yield 82%, m.p. 134.5°–135.5° C.).

F. 9-FLUORO-11-(1-ETHOXYCARBONYL-4-PIPERIDYLIDENE)-6,11-DIHYDRO-5H-BENZO[5,6]CYCLOHEPTA[1,2-b]PYRIDINE

Stir a solution of the title compound of Preparative Example 2E above (5.0 g, 16.2 mmol) and triethylamine (2.6 g, 26 mmol) in dry toluene (60 mL) at 80° C. under an argon atmosphere, and add ethylchloroformate (9.8 g, 90 mmol) via a syringe. Stir the reaction at this temperature for 30 minutes and at room temperature for one hour. Filter the reaction and remove the solvent. Pass the residue through a coarse $SiO_2$ column (60–200 mesh), and elute with $CHCl_3$ to yield the title compound as a white solid. (4.5 g, Yield 76%, m.p. 112°–114° C. after trituration with pentane).

G. 9-FLUORO-11-(4-PIPERIDYLIDENE)-6,11-DIHYDRO-5H-BENZO[5,6]CYCLOHEPTA[1,2-b]PYRIDINE

Reflux the title compound of Preparative Example 2F above (3.83 g, 10.4 mmol) with KOH (4.6 g) in 50 mL of ethanol/$H_2O$ (1:1) for 4 hours under an argon atmosphere. Pour the reaction mixture into a brine solution and extract with ethyl acetate (2×), dry over $Na_2SO_4$ and filter. Remove the solvent to give the title compound (2.86 g, Yield 90%, m.p. 138°–140° C.).

By employing the appropriately substituted benzyl halide listed in Table II in place of 4-fluorobenzylchloride in step 2A above, the desired products shown in the second column of Table 2 are prepared by employing basically the same process as described in steps 2A–2F. Workup time is determined by either TLC or HPLC. In some instances purification of the product by chromatography is necessary.

TABLE II
Product of Step G

| Benzyl Halide | | Product Melting Point |
|---|---|---|
| ClCH₂–C₆H₃(Cl) | X = H, Y = Cl | 134–135° C.[a] |
| ClCH₂–C₆H₃(F) | X = H, Y = F | 138–140° C.[b] |
| BrCH₂–C₆H₃(F)(F) | X = F, Y = F | 120–122° C.[b] |

[a] Recrystallized from ethyl acetate and pentane.
[b] Triturated with pentane.

EXAMPLE 1

8-CHLORO-11-(1-METHOXYACETYL-4-PIPERIDYLIDENE)-6,11-DIHYDRO-5H-BENZO[5,6]-CYCLOHEPTA[1,2-b]-PYRIDINE

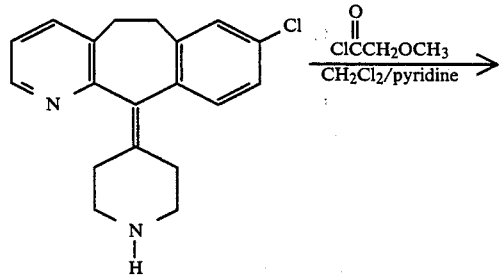

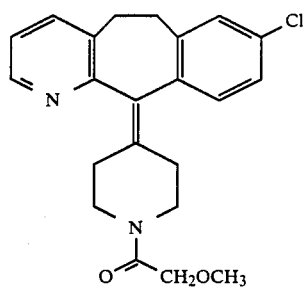

Dissolve the title compound of Preparative Example 1G above, 8-chloro-11-(4-piperidylidene)-6,11-dihydro-5H-benzo[5,6]cyclohepta[1,2-b]pyridine (3.00 gm, 9.7 mmol) and 1.2 mL (14.8 mmol) of pyridine in dry methylene chloride (20 mL) at 0° C. under an argon atmosphere. Add methoxyacetyl chloride (1.1 mL, 12.0 mmol) dropwise, and slowly warm to room temperature. After 1.5 hours take up the mixture in methylene chloride and wash with brine. Dry over $Na_2SO_4$, filter, and concentrate in vacuo to give a residue and purify via flash chromatography. Triturate the product with pentane and recrystallize from ethyl acetate/pentane to give the title compound as a white solid. (1.89 g, Yield 66%, m.p. 104°–106° C.).

EXAMPLE 2

8 OR 9-SUBSTITUTED-11-(1-SUBSTITUTED-4-PIPERIDYLIDENE)-6,11-DIHYDRO-5H-BENZO[5,6]-CYCLOHEPTA[1,2-b]-PYRIDINE COMPOUNDS

By substituting the acid halide and amine listed in the first and second columns of Table III below for the methoxyacetyl chloride and compound of Preparative Example 1G, respectively in the process described in Example 1 above the product compounds listed in the third column of Table III are prepared. Workup times are determined by monitoring the reaction by TLC. Reaction times and temperatures vary slightly. In some instances purification of the product by chromatography is not necessary.

TABLE III

| Acid Halide ClCO—R, R = | Amine X = | Y = | Product (X and Y same as in Amine) R = | Z = | Product Melting Point °C. | Comments |
|---|---|---|---|---|---|---|
| —C₆H₅ | —Cl | —H | —C₆H₅ | O | — | glassy solid |
| —CH₃ | —Cl | —H | —CH₃ | O | 155–157° C.[a] | — |
| —C(CH₃)₃ | —Cl | —H | —C(CH₃)₃ | O | 158–160° C.[b] | |
| —CH₂C(CH₃)₃ | —Cl | —H | —CH₂C(CH₃)₃ | O | 137–139° C.[b] | |

TABLE III-continued

Amine structure and Product structure (with piperidine N-CO-R group, Z=O or S)

| Acid Halide ClCO—R, R = | X = | Y = | R = (X and Y same as in Amine) | Z = | Product Melting Point °C. | Comments |
|---|---|---|---|---|---|---|
| ![2,3,4-trimethoxyphenyl] (2,3,4-(OCH₃)₃-C₆H₂—) | —Cl | —H | 2,3,4-(OCH₃)₃-C₆H₂— | O | 178–180° C.[b] | |
| —CO₂C₂H₅ | —Cl | —H | —CO₂C₂H₅ | O | 126–128° C.[c] | |
| cyclopropyl | —Cl | —H | cyclopropyl | O | — | |
| —CH₂CH₂CH₃ | —Cl | —H | —CH₂CH₂CH₃ | O | 119–122° C.[d] | |
| —SC₂H₅ | —Cl | —H | —SC₂H₅ | O | 167.5–168.5° C.[c] | triturated from pentane after flash chromatography |
| —C₂H₅ | —Cl | —H | —C₂H₅ | O | 128–130° C.[a] | |
| —CH₂OC₂H₅ | —Cl | —H | —CH₂OC₂H₅ | O | 107–109° C. | triturated from isopropyl ether after flash chromatography |
| —CH(CH₃)OCH₃ | —Cl | —H | —CHOCH₃ <br>     CH₃ | O | 128–130° C.[c,d] | |
| —C(O)CH₃ | —Cl | —H | —C(O)CH₃ | O | 150–152° C.[c] | |
| —CH₂OCH₃ | —H | —Cl | —CH₂OCH₃ | O | 104–107° C.[c] | |
| —CH₂OCH₃ | —CH₃ | —H | —CH₂OCH₃ | O | — | glassy solid |
| —CH₂OCH₃ | —H | —H | —CH₂OCH₃ | O | 87–89° C. | |
| —CH₂OCH₃ | —F | —H | —CH₂OCH₃ | O | 114–116° C.[c] | |
| —CH₂CH₂CH₃ | —F | —H | —CH₂CH₂CH₃ | O | 123–125° C. | |
| —CH₂OCH₃ | —H | —F | —CH₂OCH₃ | O | 113–115° C.[c] | |
| —CH₃ | —H | —F | —CH₃ | O | — | glassy solid |
| —CH₃ | —F | —H | —CH₃ | O | — | glassy solid |
| —CH₂OCH₃ | —F | —F | —CH₂OCH₃ | O | 151–152° C.[c] | |
| —C(O)CH₃ | —Cl | —H | —CH(OH)CH₃[e] | O | — | glassy solid |
| —C₆H₅ | —Cl | —H | —C₆H₅ | S | 147–150° C.[f] | [g] |
| —CH₃ | —CH₃ | —H | —CH₃ | O | — | glassy solid |
| —CH₃ | —Cl | —Cl | —CH₃ | O | 177–179° C. | |
| —CH₃ | —Cl | —H | —CH₃ | S | 153–155° C. | [g] |
| —CH₃ | —OCH₃ | —H | —CH₃ | O | — | glassy solid |
| —CH₃ | —H | —Cl | —CH₃ | O | — | glassy solid |
| —CH₃ | —F | —F | —CH₃ | O | 188–189° C. | |
| —CH₃ | —H | —H | —CH₃ | O | 155–156° C. | |
| —C₆H₅ (phenyl) | —H | —H | —C₆H₅ | O | 207–208° C. | |
| —CH₂—(3-Cl-C₆H₄) | —H | —H | —CH₂—(3-Cl-C₆H₄) | O | 157–158° C. | |

TABLE III-continued

| | Amine | | Product (X and Y same as in Amine) | | Product Melting Point | |
|---|---|---|---|---|---|---|
| Acid Halide ClCO—R, R = | X = | Y = | R = | Z = | °C. | Comments |
| 2,6-dimethoxyphenyl (OCH₃ groups at 2,6 positions) | —H | —H | 2,6-dimethoxyphenyl (OCH₃ groups at 2,6 positions) | O | 138–141° C. | |

[a] Recrystallized from acetone and pentane.
[b] Recrystallized from ethylacetate and isopropylether.
[c] Recrystallized from ethylacetate and pentane.
[d] Recrystallized from isopropyl ether.
[e] Following reduction with NaBH₄ in methanol.
[f] Recrystallized with ethylacetate and diethylether.
[g] The Z═O compound produced is converted to the Z═S compound by a conventional sulfuration reaction employing Lawesson's reagent.

EXAMPLE 3

8-CHLORO-11-(1-ACETYL-4-PIPERIDYLIDENE)-6,11-DIHYDRO-5H-BENZO[5,6]-CYCLOHEPTA[1,2-b]PYRIDINE

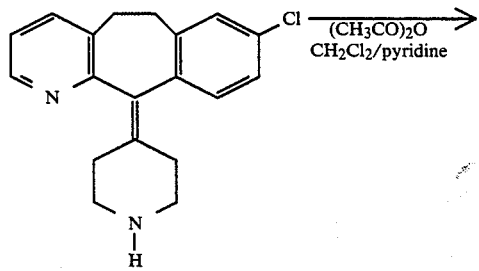

An alternate method of making the title compound is to dissolve the title compound of Preparative Example 1G (3.02 g., 9.72 mmole) and pyridine (3.9 mL, 48.1 mmol) in dry methylene chloride (40 mL) at 0° C. under an argon atmosphere and add dropwise acetic anhydride (4.5 mL, 47.7 mmole). Slowly warm the reaction mixture to room temperature. After 2 hours, take up the mixture in methylene chloride, wash with water (2×) and with brine. Dry the mixture over sodium sulfate, filter and concentrate in vacuo to give a product which is recrystallized from acetone and pentane to give the title compound as a white solid. (2.41 gm, Yield 70%, m.p. 155–157° C.).

EXAMPLE 4

8-CHLORO-11-(1-TRIFLUOROACETYL-4-PIPERIDYLIDENE)-6,11-DIHYDRO-5H-BENZO[5,6]CYCLOHEPTA[1,2-9 PYRIDINE

Substitute trifluoroacetic anhydride for acetic anhydride in the process described in Example 3 above to yield the title compound which is triturated with pentane to yield the title compound as a white solid. (m.p. 142°–144° C.).

EXAMPLE 5

8-CHLORO-11-[1-(ETHOXYCARBONYLMETHYL)-4-PIPERIDYLIDENE]-6,11-DIHYDRO-5H-BENZO[5,6]-CYCLOHEPTA[1,2-b]PYRIDINE

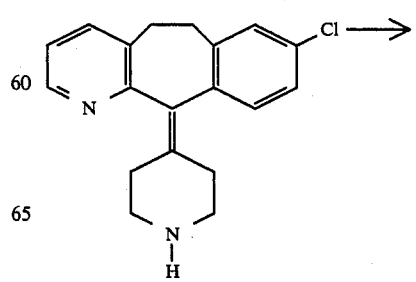

-continued

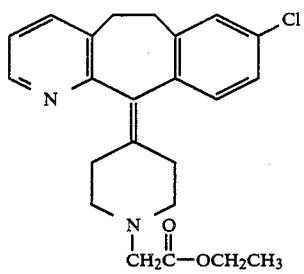

Dissolve the title compound of Preparative Example 1G (3.0 g., 9.7 mmol) in triethylamine (2.0 mL, 14.3 mmol), toluene (20 mL) and tetrahydrofuran (10 mL) at room temperature uder an argon atmosphere. Add dropwise ethylbromoacetate (1.30 mL, 11.7 mmol). After 1.5 hours, filter the mixture and concentrate in vacuo. Purify the residue via flash chromatography. Triturate the product with pentane and recrystallize from isopropylether to give the title compound as a white solid. (2.5 gms, Yield 65%, m.p. 80°–82° C.).

EXAMPLE 6

Substitute the appropriate halide and amine from Table IV below into the process of Example 5 to yield the product compounds listed in column 3 of Table IV. The workup time is determined by monitoring the reaction by TLC. The reaction time and temperature vary slightly. In some instances purification of the product by chromatography is not necessary.

EXAMPLE 7

8-CHLORO-11-[1-(t-BUTOXYCAR-BONYLAMINOACETYL)-4-PIPERIDYLIDENE]-6,11-DIHYDRO-5H-BENZ-O-5,6]CYCLOHEPTA[1,2-9 PYRIDINE

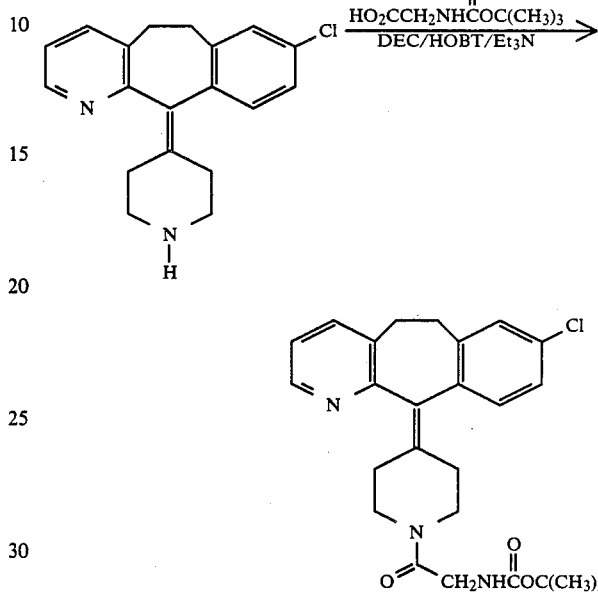

Dissolve N-t-butoxycarbonylglycine (1.84 g, 10.5 mmol), 1-(3-dimethylaminopropyl)-3-ethylcarbodiimide hydrochloride (DEC) (2.80 g, 14.6 mmol), 1-hydroxybenzotriazole hydrate (HOBT) (1.98 g, 14.7 mmol), in triethylamine (Et₃N) (2.0 mL, 14.3 mmol) and dry methylene chloride (30 mL) at 0° C. and under an argon atmosphere. Add dropwise a solution of the title compound from Preparative Example 1G (3.0 g., 9.7 mmol) in dry methylene chloride (15 mL). After 1.5 hours, take up the mixture in methylene chloride and wash with water and then with brine. Dry over sodium sulfate, filter and concentrate in vacuo to give an oil

TABLE IV

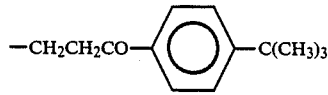

| Halide ClCH₂R R = | Amine | Product | Comments |
|---|---|---|---|
| —CH₂OCH₃CH₂OH | X = Cl, Y = H | X = Cl, Y = H, Z = H₂<br>R = —CH₂OCH₂CH₂OH | glassy solid[a] |
| —CH₂CH₂CO—⟨⟩—C(CH₃)₃ | X = Cl, Y = H, | X = Cl, Y = H, Z = H₂<br>R = —CH₂CH₂CH(OH)—⟨⟩—C(CH₃)₃ | glassy solid[b] |

[a]Reaction utilizes KI and K₂CO₃ in toluene; Reflux 8 hours.
[b]Obtained by reduction of the precursor ketone with NaBH₄ in methanol.

which is purified with flash chromatography (5% MeOH in CHCl₃). Recrystallize the purified product from ethyl acetate and pentane to give the title compound as a white solid. (4.15 gm, Yield 91%, m.p. 209°–211° C.).

EXAMPLE 8

8-CHLORO-11-(1-AMINOACETYL-4-PIPERIDYLIDENE)-6,11-DIHYDRO-5H-BENZO[5,6]CYCLOHEPTA[1,2-]PYRIDINE

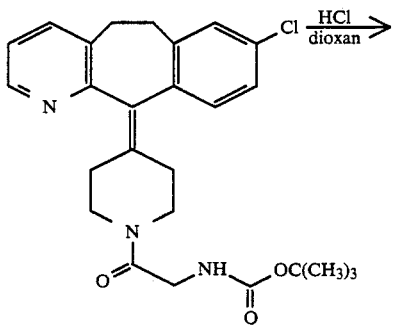

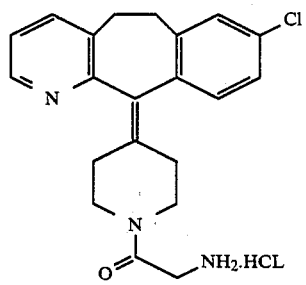

Mix the title compound of Example 7 (2.50 g., 5.34 mmol) in a saturated hydrogen chloride solution in dioxan (35 mL), and stir at room temperature under an arqon atmosphere overnight. Concentrate the mixture in vacuo and triturate the resultant gummy product with ethanol and diethylether to give the title compound as a white solid. (2.28 g., Yield 93%).

EXAMPLE 9

8-CHLORO-11-(1-FORMYL-4-PIPERIDYLIDENE)-6,11-DIHYDRO-5H-BENZO[5,6]CYCLOHEPTA[1,2-b]PYRIDINE

Dissolve the title compound of Preparative Example 1G (5.0 g., 16.1 mmol) in 100 mL of ethyl formate and reflux the mixture for 4 hours. Concentrate the mixture in vacuo and triturate the product with hexane to give the title compound as a white solid (2.2 gm, 40% yield, m.p. 147°–149° C.).

The following are examples of pharmaceutical dosage forms which contain a compound of the invention. As used therein, the term "active compound" is used to designate the compound 8-chloro-11-(1-acetyl-4-piperidylidene)-6,11-dihydro-5H-benzo[5,6]cyclohepta-[1,2-b]pyridine. The scope of the invention in its pharmaceutical composition aspect is not to be limited by the examples provided, since any other compound of structural formula I can be substituted into the pharmaceutical composition examples.

Pharmaceutical Dosage Form Examples

EXAMPLE A

| No. | Ingredient | Tablets mg/tablet | mg/tablet |
|---|---|---|---|
| 1. | Active Compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix item nos. 1 and 2 in a suitable mixer for 10–15 minutes. Granulate the mixture with item no. 3. Mill the damp granules through a coarse screen (e.g. ¼") if needed. Dry the damp granules. Screen the dried granules if needed and mix with item no. 4 and mix for 10–15 minutes. Add item no. 5 and mix for 1–3 minutes. Compress the mixture to appropriate size and weight on a suitable tablet machine.

EXAMPLE B

| No. | Ingredient | Capsules mg/capsule | mg/capsule |
|---|---|---|---|
| 1. | Active Compound | 100 | 500 |
| 2. | Lactose USP | 106 | 123 |
| 3. | Corn Starch, Food Grade, | 40 | 70 |
| 4. | Magnesium Stearate NF | 4 | 7 |
|  | Total | 250 | 700 |

Method of Manufacture

Mix item nos. 1, 2 and 3 in a suitable blender for 10–15 minutes. Add item no. 4 and mix for 1–3 minutes. Fill the mixture into suitable two-piece hard gelatin capsules on a suitable encapsulating machine.

While the present invention has been described in connection with certain specific embodiments thereof, it will be evident to one of ordinary skill in the art that many alternatives, modifications and variations may be made. All such alternatives, modifications and variations are intended to be included within the spirit and scope of the invention.

We claim:

1. A compound having the structural formula I

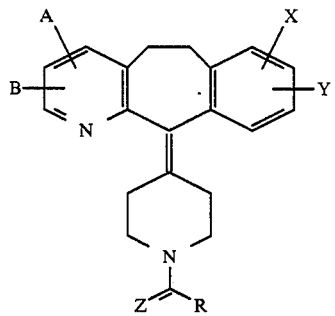

or a pharmaceutically acceptable salt or solvate thereof, wherein:

A, B, X and Y may be the same or different and each independently represents —H, halo, —CF$_3$, alkyl {which may be substituted with halo, OR$^1$ or COOR$^1$}, —OR$^1$, -13 COR$^1$, —SR$^1$, —N(R$^1$)$_2$, —NO$_2$, —O(CO)R$^1$, —COOR$^1$, or —O(CO)OR$^1$ (where each R$^1$ independently represents hydrogen, alkyl or aryl, said aryl group being an aromatic carbocyclic group having from 6 to 15 carbon atoms, said carbocyclic group being unsubstituted or substituted with a least one of halo, alkyl, hydroxy, alkoxy, phenoxy, amino, alkylamino, dialkylamino, —COOR$^1$ or —NO$_2$);

Z represents O or S, such that:

(a) when Z represents O, R represents H, aryl (wherein aryl is defined as above), —D {wherein D represents a heterocycloalkyl group selected from 2- or 3-tetrahydrofuranyl, 2- or 3-tetrahydrothienyl, 2-, 3-, or 4- piperidinyl, 2- or 3- pyrrolidinyl, 2- or 3-piperizinyl, and 2- or 4- dioxanyl or D is a group selected from

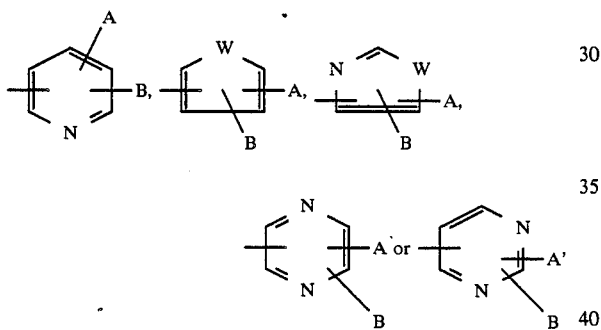

and W represents O, S, or NR$^1$ (wherein R$^1$ is defined above)}, —SR$^2$ (wherein R$^2$ represents alkyl or aryl as defined above), alkyl, cycloalkyl, alkenyl or alkynyl {which alkyl, cycloalkyl, alkenyl or alkynyl group may be unsubstituted or substituted with from 1 to 3 groups, each independently selected from halo, CON(R$^1$)$_2$, aryl as defined above, —COOR$^1$, —OR$^3$, —SR$^3$, —N(R$^1$)$_2$, —COR$^3$, —NO$_2$ or —D, wherein R$^1$ and D are as previously defined and R$^3$ represents —R$^1$, —(CH$_2$)$_m$—OR$^1$ (wherein m=1, 2, 3, or 4) or —(CH$_2$)$_n$COOR$^1$ (wherein n represents 0, 1, 2, 3 or 4), with the proviso that said alkenyl or alkynyl group does not contain a —OH, —SH or —N(R$^1$)$_2$ group on a carbon atom of the carbon-carbon double bond or carbon-carbon triple bond, respectively, thereof}; and (b) when Z represents S, R represents in addition to those R groups as defined in (a) above, aryloxy (wherein aryl is as defined above) or alkoxy.

2. A compound having the structural formula I

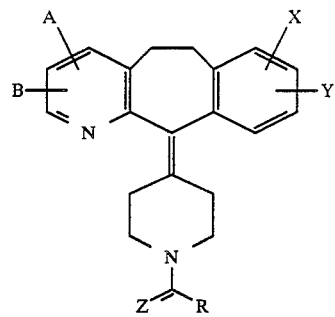

or a pharmaceutically acceptable salt or solvate thereof, wherein:

A, B, X and Y may be the same or different and each independently represents —H, halo, —CF$_3$, alkyl {which may be substituted with halo, OR$^1$ or COOR$^1$}, —OR$^1$, —COR$^1$, —SR$^1$, —N(R$^1$)$_2$, —NO$_2$, —O(CO)R$^1$, —COOR$^1$, or —O(CO)OR$^1$ (where each R$^1$ independently represents hydrogen, alkyl or aryl, said aryl group being an aromatic carbocyclic group having from 6 to 15 carbon atoms, said carbocyclic group being unsubstituted or substituted with at least one of halo, alkyl, hydroxy, alkoxy, phenoxy, amino, alkylamino, dialkylamino, —COOR$^1$ or —NO$_2$);

Z represents O or S, such that (a) when Z represents O, R represents H, aryl as defined above, —SR$^2$, alkyl, cyclocalkyl, alkenyl or alkynyl, which alkyl, cycloalkyl, alkenyl and alkynyl may optionally be substituted with from 1 to 3 groups, each independently selected from halo, C(O)N(R$^1$)$_2$, aryl, —CO$_2$R$^1$, —OR$^3$, —SR$^3$, —N(R$^1$)$_2$, —C(O)R$^3$ or —NO$_2$, where R$^1$ is as previously defined, R$^2$ is alkyl or aryl as defined above, and R$^3$ represents R$^1$, —(CH$_2$)$_m$—OR$^1$ where m is 1, 2, 3, or 4) or —(CH$_2$)$_n$CO$_2$R$^1$ where n is 0, ', 2, 3, or 4, said alkenyl or alkynyl group not containing a —OH, —SH or —N(R$^1$)$_2$ on a carbon atom of the carbon-carbon double bond or carbon-carbon triple bond, respectively; and (b) when Z represents S, R represents in addition to those R groups defined above in (a), aryloxy (wherein aryl is as defined above) or alkoxy.

3. A compound according to claim 2 wherein R represents alkyl, cycloalkyl, alkenyl, aryl or alkyl substituted with OR$^3$, SR$^3$, NR$^1$R$^3$ or COR$^3$.

4. A compound according to claim 3 wherein Z is O.

5. A compound according to claim 2 wherein R represents alkyl having from 1 to 3 carbon atoms, cycloalkyl of from 3 to 6 carbon atoms, alkenyl of from 3 to 4 carbon atoms or alkyl of from 1 to 3 carbon atoms substituted with OR$^3$, SR$^3$, NR$^1$R$^3$ or COR$^3$.

6. A compound according to claim 5 wherein A, B, X and Y represent H or halo.

7. A compound according to claim 6 wherein A and B are H.

8. A compound according to claim 7 wherein X is halo and Y is H.

9. A compound according to claim 8 wherein X is chloro or fluoro.

10. A compound according to claim 9 wherein X is in the 8- or 9-position.

11. A compound according to claim 7 wherein R is alkyl of from 1 to 3 carbon atoms.

12. A compound according to claim 7 wherein R is alkyl of 1 to 3 carbon atoms and is substituted with a group OR³.

13. A compound according to claim 11 wherein R is methyl, ethyl or propyl.

14. A compound according to claim 12 wherein R is alkoxyalkyl.

15. 8-Chloro-11-(1-acetyl-4-piperidylidene)-6,11-dihydro-5H-benzo[5,6]cyclohepta [1,2-b]pyridine.

16. 8-Chloro-11-(1-methoxyacetyl-4-piperidylidene)-6,11-dihydro-5H-benzo[5,6]cyclohepta[1,2-b]pyridine.

17. 8-Chloro-11-(1-propionyl-4-piperidylidene)-6,11-dihydro-5H-benzo[5,6]cyclohepta[1,2-b]pyridine.

18. 8-Fluoro-11-(1-acetyl-4-piperidylidene)-6,11-dihydro-5H-benzo[5,6]cyclohepta[1,2-b]pyridine.

19. 9-Fluoro-11-(1-acetyl-4-piperidylidene)-6,11-dihydro-5H-benzo[5,6]cyclohepta[1,2-b]pyridine.

20. An antiallergic or antiinflammatory pharmaceutical composition which comprises an antiallergic or antiinflammatory effective amount of a compound having structural formula I as defined in claim 1 in combination with a pharmaceutically acceptable carrier.

21. A method of treating allergy in a mammal comprising administering to said mammal an anti-allergic effective amount of a compound according to claim 1.

22. A method for treating inflammation in a mammal comprising administering to said mammal an anti-inflammatory effective amount of a compound according to claim 1.

23. An anti-allergy or anti-inflammatory pharmaceutical composition which comprises an effective amount of a compound of structural formula I as defined in claim 2 in combination with a pharmaceutically acceptable carrier.

24. A method of treating allergy in a mammal comprising administering to said mammal an anti-allergic effective amount of a compound of formula I as defined in claim 2.

25. A method of treating inflammation in a mammal comprising administering to said mammal an anti-inflammatory effective amount of a compound of formula I as defined in claim 2.

26. A compound having the following name:
11-(1-acetyl-4-piperidylidene)-6,11-dihydro-5H-benzo[5,6]cyclohepta[1,2-b]pyridine;
11-(1-methoxyacetyl-4-piperidylidene)-6,11-dihydro-5H-benzo[5,6]cyclohepta[1,2-b]pyridin
11-(1-benzoyl4-piperidylidene)-6,11-dihdyro-5H-benzo[5,6]cyclohepta[1,2-b]pyridine;
11-[1-(3-chlorophenylacetyl)-4--piperidylidene]6,11-dihydro-5H-benzo[5,6]cyclohepta[
11-[1-(3,4-dimethoxybenzyol)-4-piperidylidene]6,11-dihydro-5H-benzo[5,6]cyclohepta[1,2-b]pyridine;
8-chloro-11-(1-acetyl-4-piperidylidene)-6,11-dihydro-5H-benzo[5,6]cyclohepta[1,2-b]pyridine;
8-chloro-11-(1-propionyl-4-piperidylidene)-6,11-dihydro-5H-benzo[5,6]cyclohepta[1,2-b]pyridine;
8-chloro-11-(1-trimethylacetyl-4-piperidylidene)-6,11-dihydro-5H-benzo[5,6]cyclohepta[1,2-b]pyridine;
8-chloro-11-[1-(tertiary butylacetyl-4-piperidylidene]-6,11-dihyro-5H-benzo[5,6]cyclohepta [1,2-b]pyridine;
8-chloro-11-(1-methoxyacetyl-4-piperidylidene)-6,11-dihydro-5H-benzo[5,6]cyclohepta [1,2-b]pyridine;
8-chloro-11-[1-(ethoxyacetyl)-4-piperidylidene]-6,11-dihydro-5H-benzo[5,6]cyclohepta [1,2-b]pyridine;
8-chloro-11-[1-(2-hydroxypropionyl-4-piperidylidene]-6,11-dihydro-5H-benzo[5,6]cyclohepta [1,2-b]pyridine;
9-chloro-11-(1-methoxyacetyl-4-piperidylidene)-6,11-dihydro-5H-benzo[5,6]cyclohepta [1,2-b]pyridine;
8-chloro-11-[1-(2-methoxypropionyl)-4-piperidylidene]-6,11-dihydro-5H-benzo[5,6]cyclohepta[1,2-b]pyridine;
8-chloro-11-[1-(1,2-propanedionyl)-4-piperidylidene]-6,11-dihydro-5H-benzo[5,6]cyclohepta [1,2-b]pyridine;
8-chloro-11-[1-(1-ethoxyoxoacetyl)-4-piperidylidene]-6,11-dihydro-5H-benzo[5,6]cyclohepta [1,2-b]pyridine;
8-chloro-11-[1-(tertiary butoxycarbonylaminoacetyl)-4-piperidylidene]-6,11-dihdyro-5H-benzo[5,6]cyclohepta[1,2-b]pyridine;
8-chloro-11-(1-trifluoroacetyl-4-piperidylidene)-6,11-dihydro-5H-benzo[5,6]cyclohepta [1,2-b]pyridine;
8-chloro-11-(1-benzoyl-4-piperidylidene)-6,11-dihydro-5H-benzo[5,6]cyclohepta[1,2-b]pyridine;
8-chloro-11-[1-(3,4,5-trimethoxybenzoyl)-4-piperidylidene]-6,11-dihydro-5H-benzo[5,6]cyclohepta[1,2-b]pyridine;
8-fluoro-11-(1-acetyl-4-piperidylidene)-6,11-dihydro-5H-benzo[5,6]cyclohepta[1,2-b]pyridine;
8-fluoro-11-(1-butyryl-4-piperidylidene)-6,11-dihydro-5H-benzo[5,6]cyclohepta[1,2-b]pyridine;
8-fluoro-11-(1-methoxyacetyl-4-piperidylidene)-6,11-dihydro-5H-benzo[5,6]cyclohepta[1,2-b]pyridine;
9-fluoro-11-(1-acetyl-4-piperidylidene)-6,11-dihydro-5H-benzo[5,6]cyclohepta[1,2-b]pyridine;
9-fluoro-11-(1-methoxyacetyl-4-piperidylidene)-6,11-dihydro-5H-benzo[5,6]cyclohepta[1,2-b]pyridine;
8,9-difluoro-11-(1-methoxyacetyl-4-piperidylidene)-6,11-dihydro-5H-benzo[5,6]cyclohepta [1,2-b]pyridine;
8-methyl-11-(1-methoxy-acetyl-4-piperidylidene)-6,11-dihydro-5H-benzo[5,6]cyclohepta[1,2-b]pyridine;
8-chloro-11-(1-cyclopropylcarbonyl-4-piperidylidene)-6,11-dihydro-5H-benzo[5,6]cyclohepta[1,2-b]pyridene;
8-chloro-11-(1-butyryl-4-piperidylidene)-6,11-dihydro-5H-benzo[5,6]cyclohepta[1,2-b]pyridine;
8-methoxy-11-(1-acetyl-4-piperidylidene)-6,11-dihydro-5H-benzo[5,6]cyclohepta[1,2-b]pyridine;
9-chloro-11-(1-acetyl-4-piperidylidene)-6,11-dihydro-5H-benzo[5,6]cyclohepta[1,2-b]pyridine;
8,9-difluoro-11-(1-acetyl-4-piperidylidene)-6,11-dhhydro-5H-benzo[5,6]cyclohepta[1,2-b]pyridine;
8-methyl-11-(1-acetyl-4-piperidylidene)-6,11-dihydro-5H-benzo[5,6]cyclohepta[1,2-b]pyridine;
8,9-dichloro-11-(1-acetyl-4-piperidylidene)-6,11-dihydro-5H-benzo[5,6]cyclohepta[1,2-b]pyridine;
8-chloro-11-(1-aminoacetyl-4-piperidylidene)-6,11-dihydro-5H-benzo[5,6]cyclohepta[1,2-b]pyridine;
8-chloro-11-(1-formyl-4-piperidylidene)-6,11-dihydro-5H-benzo[5,6]cyclohepta[1,2-b]pyridine;
8-chloro-11-(1-phenylthioxomethyl-4-piperidylidene)-6,11-dihydro-5H-benzo[5,6]cyclohepta[1,2-b]pyridine;
8-chloro-11---6,11-dihydro-5H-benzo[5,6]cyclohepta[1,2-b]pyridine; or
8-chloro-11-[1-(ethylthio)carbonyl]-4-piperidylidene]-6,11-dihydro-5H-benzo[5,6]cyclohepta[1,2-b]pyridine.

27. A compound having the structural formula I

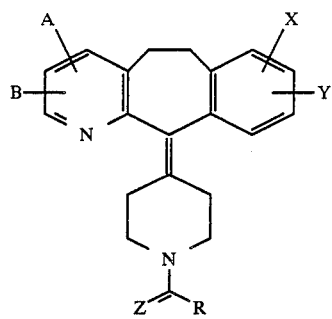

or a pharmaceutically acceptable salt or solvate thereof, wherein:

A, B, X and Y may be the same or different and each independently represents —H, halo, —CF$_3$, alkyl having from 1 to 6 carbons {which alkyl group may be substituted with halo, OR$^1$ or COOR$^2$}, —OR$^1$, —COR$^1$, —SR$^1$, —N(R$^1$)$_2$, —O(CO)R$^1$ or —COOR$^1$ (where each R$^1$ independently represents hydrogen, alkyl or aryl, said aryl group being an aromatic carbocyclic group having from 6 to 15 carbon atoms, said carbocyclic group being unsubstituted or substituted with at least one of halo, alkyl, hydroxy, alkoxy, phenoxy, amino, alkylamino, dialkylamino, —COOR$^1$ or —NO$_2$);

Z represents O or S; and

R represents H, aryl as defined above, —D {wherein D represents a heterocycloalkyl group selected from 2- or 3-tetrahydrofuranyl, 2- or 3-tetrahydrothienyl, 2-, 3-, or 4-piperidinyl, 2- or 3-pyrrolidinyl, 2- or 3-piperizinyl, and 2- or 4-dioxanyl or D is a group selected from

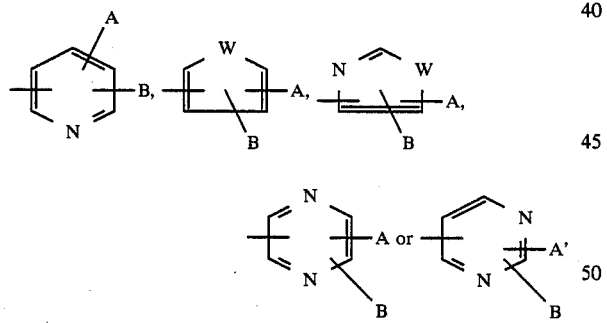

and W represents O, S, or NR$^1$ (wherein R$^1$ is defined above)}, alkyl having from 1 to 6 carbons, cycloalkyl having from 1 to 6 carbons, alkenyl having from 2 to 6 carbons, or alkynyl having from 2 to 6 carbons {which alkyl, cycloalkyl, alkenyl or alkynyl group may be unsubstituted or substituted with from 1 to 3 groups, each independently selected from —OR$^1$, —SR$^1$, —N(R$^1$)$_2$ or —D, wherein R$^1$ and D are as previously defined with the proviso that said alkenyl or alkynyl group does not contain a —OH, —SH or —N(R$^1$)$_2$ group on a carbon atom of the carbon-carbon double bond or carbon-carbon triple bond, respectively thereof}.

28. A compound having the structural formula I

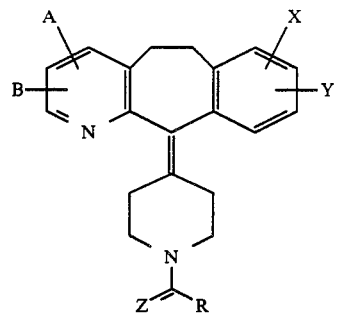

or a pharmaceutically acceptable salt or solvate thereof, wherein:

A, B, X and Y may be the same or different and each independently represents —H, halo, —CF$_3$, alkyl having from 1 to 6 carbons, —OR$^1$, —SR$^1$ or —N(R$^1$)$_2$ (where each R$^1$ independently represents hydrogen or alkyl);

Z represents O; and

R represents H, —D {wherein D represents a heterocycloalkyl group selected from 2- or 3-tetrahydrofuranyl, 2- or 3-tetrahydrothienyl, 2-, 3-, or 4-piperidinyl, 2- or 3-pyrrolidinyl, 2- or 3-piperizinyl, and 2- or 4-dioxanyl or D is

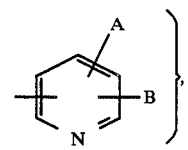

alkyl having from 1 to 6 carbon atoms, or cycloalkyl having from 1 to 6 carbon atoms {which alkyl or cycloalkyl group may be unsubstituted or substituted with from 1 to 3 groups, each independently selected from —OR$^1$, —SR$^1$ or —D, wherein R$^1$ and D are as previously defined}.

29. A compound having the structural formula I

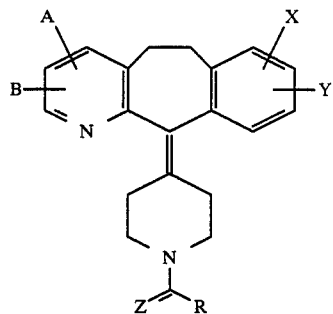

or a pharmaceutically acceptable salt or solvate thereof, wherein:

A, B, X and Y may be the same or different and each independently represents —H, halo, —CF$_3$, alkyl having from 1 to 6 carbons {which may be unsubstituted or substituted with halo, OR$^1$ or COOR$^1$}, —OR$^1$, —COR$^1$, —SR$^1$, —N(R$^1$)$_2$, —O(CO)R$^1$ or —COOR$^1$ (where each R$^1$ independently represents hydrogen, alkyl or aryl, said aryl group being an aromatic carbocyclic group having from 6 to 15 carbon atoms, said carbocyclic group being unsubstituted or substituted with at least one of halo, alkyl, hydroxy, alkoxy, phenoxy, amino, alkylamino, dialkylamino, —COOR$^1$ or —NO$_2$);

Z represents S; and

R represents —SR$^2$ (wherein R$^2$ represents alkyl or aryl as defined above), aryloxy (wherein aryl is as defined above) or alkoxy.

* * * * *

UNITED STATES PATENT AND TRADEMARK OFFICE
Certificate

Patent No. 4,826,853

Patented: May 2, 1989

On petition requesting issuance of a certificate for correction of inventorship pursuant to 35 U.S.C. 256, it has been found that the above-identified patent, through error and without any deceptive intent, improperly sets forth the inventorship. Accordingly, it is hereby certified that the correct inventorship of this patent is:

John J. Piwinski, Ashit K. Ganguly, Michael J. Green, Frank J. Villani, Jesse Wong and Charles A. Magetti.

Signed and Sealed this Twenty-eighth Day of August 1990.

MARY LEE

*Supervisory Primary Examiner*
*Art Unit 121*